US012806390B2

(12) United States Patent
Rahimi et al.

(10) Patent No.: US 12,806,390 B2
(45) Date of Patent: Nov. 24, 2026

(54) OZONE GENERATION APPARATUSES AND METHODS OF TREATING WOUNDS

(71) Applicant: Purdue Research Foundation, West Lafayette, IN (US)

(72) Inventors: Rahim Rahimi, West Lafayette, IN (US); Babak Ziaie, Oneonta, NY (US); Alexander Roth, Upland, IN (US)

(73) Assignee: Purdue Research Foundation, West Lafayette, IN (US)

( * ) Notice: Subject to any disclaimer, the term of this patent is extended or adjusted under 35 U.S.C. 154(b) by 853 days.

(21) Appl. No.: 18/017,300

(22) PCT Filed: Jul. 23, 2021

(86) PCT No.: PCT/US2021/042872

§ 371 (c)(1),
(2) Date: Jan. 20, 2023

(87) PCT Pub. No.: WO2022/020660

PCT Pub. Date: Jan. 27, 2022

(65) Prior Publication Data

US 2023/0256217 A1 Aug. 17, 2023

Related U.S. Application Data

(60) Provisional application No. 63/055,465, filed on Jul. 23, 2020.

(51) Int. Cl.
*A61M 35/00* (2006.01)
*A61F 13/00* (2024.01)
(Continued)

(52) U.S. Cl.
CPC ....... *A61M 35/30* (2019.05); *A61F 13/00051* (2013.01); *A61L 2/20* (2013.01);
(Continued)

(58) Field of Classification Search
CPC . A61M 35/30; A61F 13/00051; A61L 2/0094; A61L 2/202; A61L 2202/11
See application file for complete search history.

(56) References Cited

U.S. PATENT DOCUMENTS 5,052,382 A * 10/1991 Wainwright ............ A61M 1/32 128/202.25
6,071,254 A * 6/2000 Augustine ............... A61M 1/85 602/41
(Continued)

FOREIGN PATENT DOCUMENTS

CA 3058866 A1 * 10/2018 ............... D01F 8/10
GB 2544813 A * 5/2017 ........... A61K 9/0002
(Continued)

OTHER PUBLICATIONS

Roth, A. et. al., "Wearable and Flexible Ozone Generating System for Treatment of Infected Dermal Wounds," Frontiers in Bioengineering and Biotchnology, May 2020, vol. 8, Article 458, (13 pages).
(Continued)

*Primary Examiner* — Cris L. Rodriguez
(74) *Attorney, Agent, or Firm* — Hartman Global IP Law; Gary M. Hartman; Domenica N.S. Hartman

(57) ABSTRACT

An ozone generation apparatus includes a flexible and porous gas permeable treatment patch configured to be releasably secured to a user's body such that an exterior surface of the treatment patch directly contacts skin on the user's body, and an ozone generating unit fluidically coupled to the treatment patch and configured to provide a flow of ozone through pores in the treatment patch toward and out through the exterior surface of the treatment patch. In certain embodiments, the patch may be used for combination therapies in which both ozone and antibiotics are simultaneously applied to the user's body.

14 Claims, 33 Drawing Sheets

(51) Int. Cl.
*A61L 2/20* (2026.01)
*A61L 2/202* (2026.01)
*A61L 103/05* (2026.01)

(52) U.S. Cl.
CPC .......... *A61L 2/202* (2013.01); *A61L 2103/05* (2026.01); *A61L 2202/11* (2013.01)

(56) References Cited

U.S. PATENT DOCUMENTS 6,810,288 B2 10/2004 Joshi
8,168,229 B2 * 5/2012 Larsen .................... A61L 15/32 602/41
9,289,193 B2 * 3/2016 Argenta ................ A61M 1/984
10,695,226 B2 * 6/2020 Collinson ............... A61F 13/05
2004/0006319 A1 * 1/2004 Lina ...................... A61M 1/962 604/304
2007/0225631 A1 * 9/2007 Bowlin .................. A61K 38/39 602/52
2008/0045874 A1 * 2/2008 An ............................ A61L 2/20 602/56
2008/0071206 A1 * 3/2008 Peters .................. A61K 9/7023 602/41
2008/0167594 A1 * 7/2008 Siniaguine ........ A61F 13/00063 602/58
2009/0137936 A1 * 5/2009 Belenkaya .............. A61P 31/04 602/43
2009/0324680 A1 * 12/2009 Reneker ................... A61K 9/00 424/423
2010/0008994 A1 * 1/2010 Reneker .................. A61P 25/26 424/489
2010/0166854 A1 * 7/2010 Michniak-Kohn ..... A61L 27/58 424/456
2010/0286639 A1 * 11/2010 Scholz .................... A61F 13/05 602/54
2010/0303881 A1 * 12/2010 Hoke ...................... A61L 27/54 424/423
2011/0021964 A1 * 1/2011 Larsen .................... A61P 17/02 602/47
2011/0045041 A1 * 2/2011 Golubovic-Liakopoulos .............. A61P 17/02 424/401
2011/0130712 A1 * 6/2011 Topaz ..................... A61M 1/74 604/23
2011/0229551 A1 * 9/2011 Doshi .................. D01D 5/0007 424/443
2011/0288458 A1 * 11/2011 Jones ................... A61H 9/0078 601/149
2012/0070485 A1 * 3/2012 Soldani ................... A61L 15/42 424/443
2012/0148493 A1 * 6/2012 Schmehl .............. A61K 9/5153 424/9.1
2012/0277662 A1 * 11/2012 Golkowski ............... A61L 2/00 422/186.21
2013/0030340 A1 * 1/2013 Vincent .............. D04H 1/43828 442/164
2013/0095167 A1 * 4/2013 Warnke ................... A61L 27/14 424/443
2013/0190672 A1 * 7/2013 Liu ......................... A61L 15/46 602/45
2013/0266664 A1 * 10/2013 Yang ...................... D04H 1/728 427/508
2014/0120057 A1 * 5/2014 Uhrich ................. A61K 31/765 424/78.37
2015/0072008 A1 * 3/2015 Tornero Garcia ....... A61K 9/70 604/289
2015/0119833 A1 * 4/2015 Coulthard ............... A61M 1/90 604/319
2016/0120706 A1 * 5/2016 Collinson ............. A61M 1/915 604/319
2016/0256638 A1 * 9/2016 Sarangapani ..... A61F 13/00063
2019/0117464 A1 4/2019 Seo et al.
2019/0388666 A1 * 12/2019 Buchegger ............ A61M 35/30
2020/0030496 A1 * 1/2020 Reddy ................. A61L 27/3834
2020/0121509 A1 * 4/2020 Locke ................. A61F 13/0223
2020/0121510 A1 * 4/2020 Hartwell ................. A61M 1/94
2020/0261629 A1 * 8/2020 Hunt ................. A61F 13/00051
2024/0215905 A1 * 7/2024 Freeman .............. G01N 27/327

FOREIGN PATENT DOCUMENTS

JP 2018530380 10/2018
RU 2596054 C2 * 8/2016 ............ A61M 1/912
WO WO-9106275 A1 * 5/1991 ............ A61H 33/14
WO WO-2010024928 A1 * 3/2010 .............. A61P 31/04

OTHER PUBLICATIONS

Sahin, H. et al., "The Acute Effects of Preoperative Ozone Theraphy on Surgical Wound Healing," Acta Cirurgica Brasileira, vol. 31, (7) 2016, pp. 472-479.

International Search Report and Written Opinion dated Nov. 10, 2021, for International Application No. PCT/US2021/042872, (9 pages).

* cited by examiner

| | | |
|---|---|---|
| 6.67 | 5 | 3.67 |
| 8.67 | 84.33 | 2.33 |
| 3.33 | 2.67 | 1.33 |

| | | |
|---|---|---|
| 17.33 | 25.33 | 12.33 |
| 25 | 75.33 | 21 |
| 18 | 31.33 | 14.67 |

OZONE GENERATION APPARATUSES AND METHODS OF TREATING WOUNDS

CROSS REFERENCE TO RELATED APPLICATIONS

This application claims priority to International Patent Application No. PCT/US2021/42872 filed Jul. 23, 2021, which claims the benefit of U.S. Provisional Application Nos. 63/055,465 filed Jul. 23, 2020. The contents of these prior patent documents are incorporated herein by reference.

BACKGROUND OF THE INVENTION

The present invention generally relates to therapeutic ozone-based wound care. The invention particularly relates to an ozone generation apparatus that includes an ozone generator and a treatment patch configured to apply ozone to a wound of a patient.

Within the healthcare industry, infections of the skin or other soft tissues are a growing cause of patient morbidity. These skin and soft tissue infections (SSTIs), which often infect pressure ulcers (PUs) or diabetic foot ulcers (DFUs) are part of the large global market for wound care. In the United States in 2016, SSTIs were the cause for 3.5% of emergency room visits and treatment costs averaged about $8,000 USD. These numbers are expected to increase even further in years to come due to the prevalence of chronic health conditions and an aging population. On a global scale, 2% of adults with diabetes are expected to develop a DFU each year. The development of a DFU adds significant cost for diabetes patients, with approximately 33% of the total cost of diabetes treatment each year being linked to them. The greatest complications for DFU patients occur when the wound becomes infected with bacteria, which statistically occurs in almost half of patients. Such infections significantly increase the cost of treatment of a DFU, and often lead to reduced healing of the wound and other conditions such as osteomyelitis, systemic infection, increased risk of amputation, and death. In fact, nearly 1% of diabetic individuals are expected to have at least one lower limb amputated during their lifetime.

Typical treatment for SSTI infections, including those in PUs and DFUs, involves administration of antibiotics. While this treatment method may be able to reduce bacterial load in many cases, it does nothing to help promote early wound healing. Additionally, bacterial resistance to antibiotics is a growing global issue that further reduces the validity of current treatment methods. This issue is even more alarming since the development and approval of new antimicrobials effective in treating multidrug-resistant pathogens has not kept pace with the continued emergence of new resistances in bacteria.

Recently, there has been increased effort toward the development of alternative (non-antibiotic) materials and treatments for bacterial infections, particularly multi-drug resistant bacterial infections. Among the most popular are the use of cold atmospheric plasma (CAP), metallic nanoparticles (NPs), and gaseous ozone. Previous research using CAP has shown that the ionized particles generated exhibit encouraging antimicrobial properties and also help promote healing factors in the wound. Unfortunately, the cost and complexity of the systems have prohibited utilization of the technology for typical treatments. Metallic NPs, such as those made from copper and silver, have also been extensively studied because of their strong antimicrobial properties. Currently, these NPs show positive signs for treatment purposes in the lab setting but are challenging to implement in practice due to high levels of cytotoxicity. Gaseous ozone, on the other hand, has been shown to be a strong, safe, and accessible alternative treatment.

For example, topical ozone therapy has shown to be a promising alternative approach for treatment of non-healing and infected wounds by providing strong antibacterial properties while stimulating the local tissue repair and regeneration. Ozone therapy is a gas phase antimicrobial therapeutic modality. Ozone is known to inactivate harmful microorganisms including bacteria, viruses, fungi, and more. This is due to its naturally strong oxidative tendencies which work to weaken the outer membrane of the bacteria cell through applied oxidative stress. In addition to its antimicrobial properties, ozone also stimulates wound healing through applied oxidative stress, which leads to increased production and migration of wound healing factors, and increased oxygen levels at the wound site. However, utilization of ozone as a treatment for infected wounds has been challenging thus far due to the need for large equipment usable only in contained, clinical settings. In addition, many of the in vitro investigations reported in the literature have focused on utilization of high concentrations of ozone (0.6-20 g/mL).

In view of the above, it can be appreciated that there are certain problems, shortcomings or disadvantages associated with ozone therapy, and that it would be desirable if systems and methods were available for treating wounds with ozone that were portable and low cost.

BRIEF DESCRIPTION OF THE INVENTION

The present invention provides ozone generation apparatuses and methods of treating wounds that are portable and potentially low cost.

According to one aspect of the invention, an ozone generation apparatus is provided that includes a flexible and porous gas permeable treatment patch configured to be releasably secured to a user's body such that an exterior surface of the treatment patch directly contacts skin on the user's body, and an ozone generating unit fluidically coupled to the treatment patch and configured to provide a flow of ozone through pores in the treatment patch toward and out through the exterior surface of the treatment patch.

According to another aspect of the invention, a method is provided for treating a wound on a patient that includes releasably securing a flexible and porous gas permeable treatment patch of an ozone generation apparatus to a user's body such that an exterior surface of the treatment patch directly contacts skin comprising the wound on the user's body, generating ozone with an ozone generating unit fluidically coupled to the treatment patch, and providing a flow of the ozone from the ozone generating unit through pores in the treatment patch toward and out through the exterior surface of the treatment patch such that the ozone contacts the wound.

Technical effects of the apparatus and method described above preferably include the capability of providing effective ozone therapy for wound care with a portable apparatus that may be used in nonclinical settings.

Other aspects and advantages of this invention will be appreciated from the following detailed description.

BRIEF DESCRIPTION OF THE DRAWINGS

FIGS. 11B, 11D, 11F, 11H).

FIG. 17A represents biocompatibility results of ozone and Linezolid adjunct therapy on *P. aeruginosa* after ozone was applied at 100 ppm for six hours and linezolid was dissolved from the nanofibers applied in solution at 20 g/mL. FIG. 17B represents biocompatibility results of ozone and vancomycin adjunct therapy on *P. aeruginosa* after ozone was applied at 100 pm for six hours and vancomycin was dissolved from the nanofibers and applied in solution at 20 g/mL.

DETAILED DESCRIPTION OF THE INVENTION

Figure 1A:
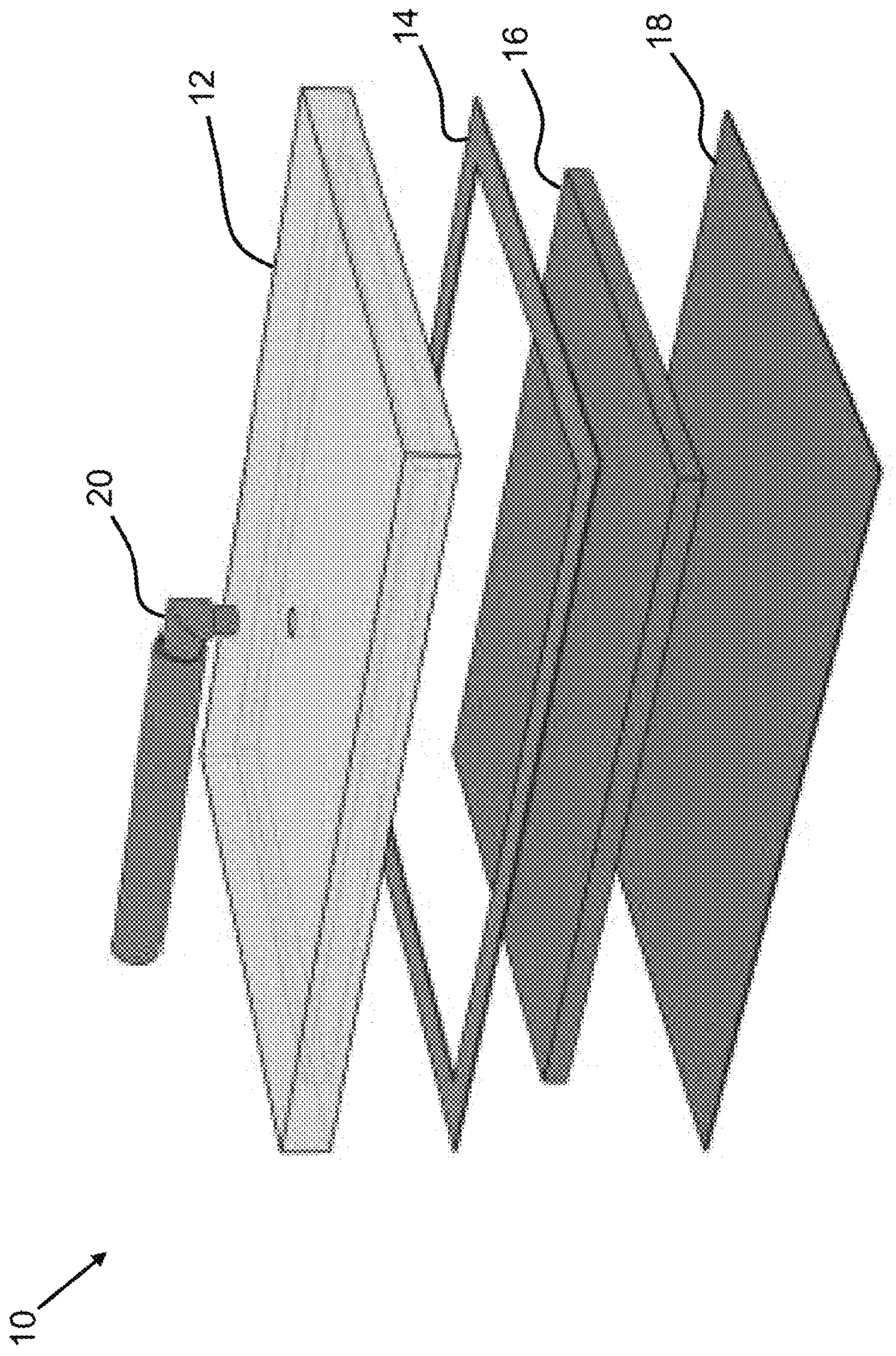
FIGS. 1A through 1C represent various layers of a non-limiting ozone treatment patch (FIG. 1A), components of a nonlimiting portable ozone treatment system (FIG. 1B), and the combined portable system attached to a belt with the patch on a patient's forearm (FIG. 1C).

Disclosed herein is a wearable, ozone generation apparatus configured for ozone treatment to be administered topically to a patient within or outside of a clinical setting. The apparatus includes a portable ozone generating unit 30 fluidically connected via a gas input tubing 50 to a flexible and porous gas permeable treatment patch 10, which in combination are configured to deliver generated ozone to a wound site 26 on a user.

Unlike certain treatment methods reported in the literature which generate high ozone concentrations using specialized gasses, the apparatus preferably generates and provides lower dose ozone treatments applied topically to only the wound site. This technology enables treatment options outside of the clinical setting, does not confine the patient to a certain location, and is capable of generating gaseous ozone from ambient surroundings. Furthermore, the convenience of the portable apparatus allows for longer treatment times such that lower dose treatments are effective. By lowering the concentration of active ozone, the apparatus also reduces the risk of dangerous levels of ozone exposure to the patient relative to previously reported treatments utilizing higher doses of ozone. As used herein, low doses or concentrations of ozone include amounts below 0.6 g/mL, preferably between 0.2 to 0.6 g/mL, and more preferably about 0.2 g/mL. Such doses may be administered for a period of time sufficient for producing a therapeutic effect. Treatments with the apparatus may be effective against various harmful organisms, and may be especially beneficial for treating multi-drug resistant infections. For instance, treatment with the apparatus may be effective at treating methicillin-resistant *Staphylococcus* aurous (MRSA).

FIG. 1A schematically represents an expanded view of a nonlimiting treatment patch 10 that includes a backing 12, a bonding layer 14, an intermediate flow dispersion layer 16, and a wound contact layer 18. Preferably, the patch 10 is formed of low-cost materials and is disposable.

For effective ozone treatment, the patch 10 preferably has uniform permeation of gas through the wound contact layer 18 without significant resistance. As a nonlimiting example, the wound contact layer 18 may be formed of a synthetic Rayon-Spandex knit fabric which would provide relatively high gas permeability at a low cost. Additionally, the wound contact layer 18 preferably exhibits hydrophobic properties to allow for contact with biofluids on the wound surface without blocking the exposed pores. To introduce hydrophobicity, an exterior surface of the wound contact layer 18 may be coated in with a hydrophobic material such as a diluted polydimethylsiloxane (PDMS) solution.

The intermediate flow dispersion layer 16 preferably promotes uniform output flow. An exemplary material for the dispersion layer 16 is a low-cost woven polymer material such as polyester batting which has a significant porosity for the gas to pass through. The presence of the dispersion layer 16 preferably provides a gradient of pore sizes, which adds a small resistance to flow and causes the flow of gas to distribute from the single, centrally located gas input connection 20 in the patch 10 toward the extremities of the patch 10 and leads to a more consistent application of ozone across the wound. The dispersion layer 16 may be encased within the backing 12.

The backing 12 provides structural support for the patch 10 and may be formed of a polymeric material such as polydimethylsiloxane (PDMS). In the embodiment represented in FIG. 1A, the wound contact layer 18 is secured to the backing 12 with the bonding layer 14 which may be, for example, an adhesive glue or double-sided adhesive tape. The backing 12 includes a gas input hole and the gas input connection 20 that may permanently or releasably couple the patch 10 to flexible tubing 50.

Figure 1B:
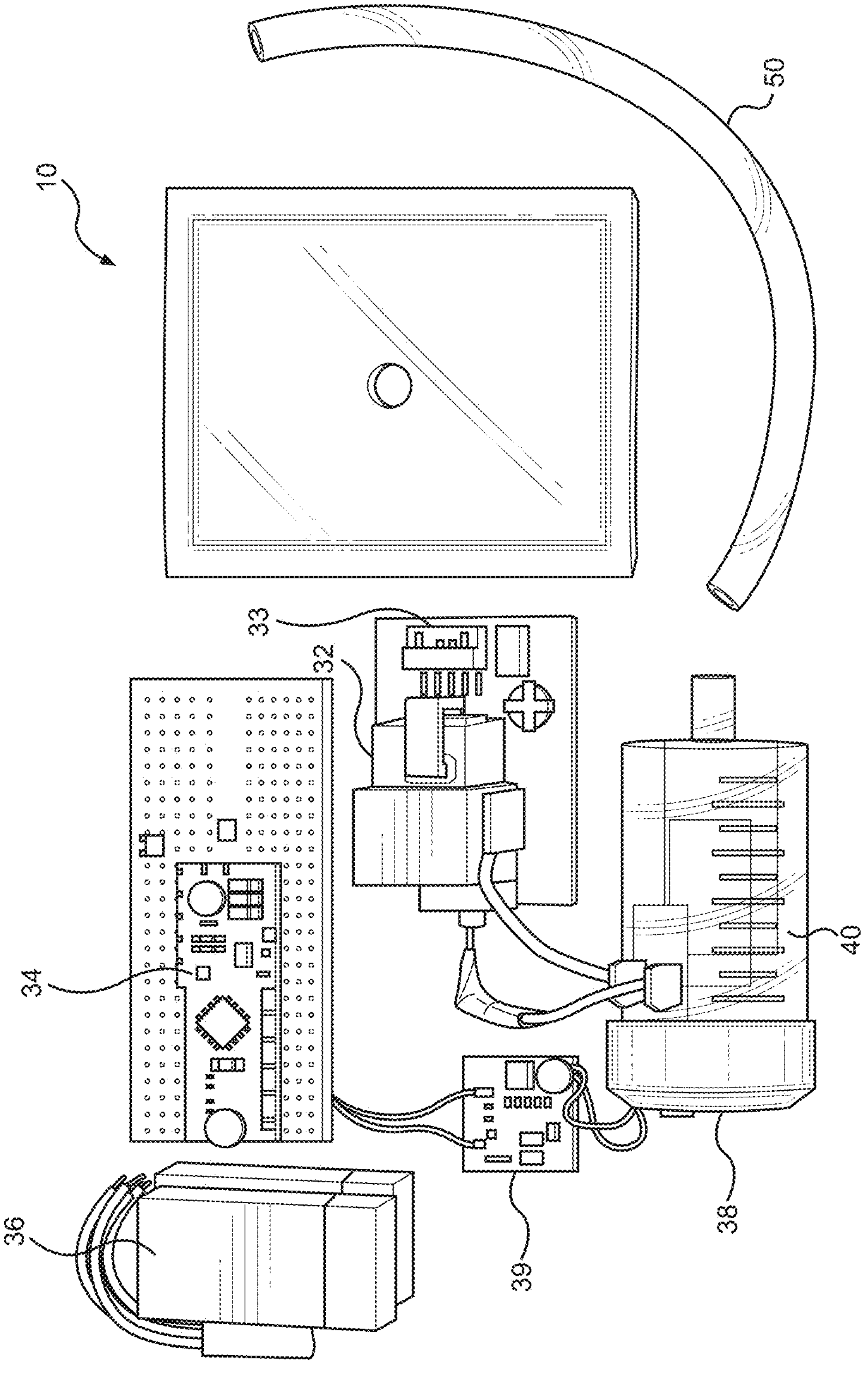

FIG. 1B represents components of a nonlimiting ozone generating unit 30 that includes a small, low voltage commercial ozone generator 32 and a micro-blower fan 38. The leads of the ozone generator 32 were enclosed in a sealed chamber 40 with an outlet connected to the patch 10 via the tubing 50.

Figure 1C:
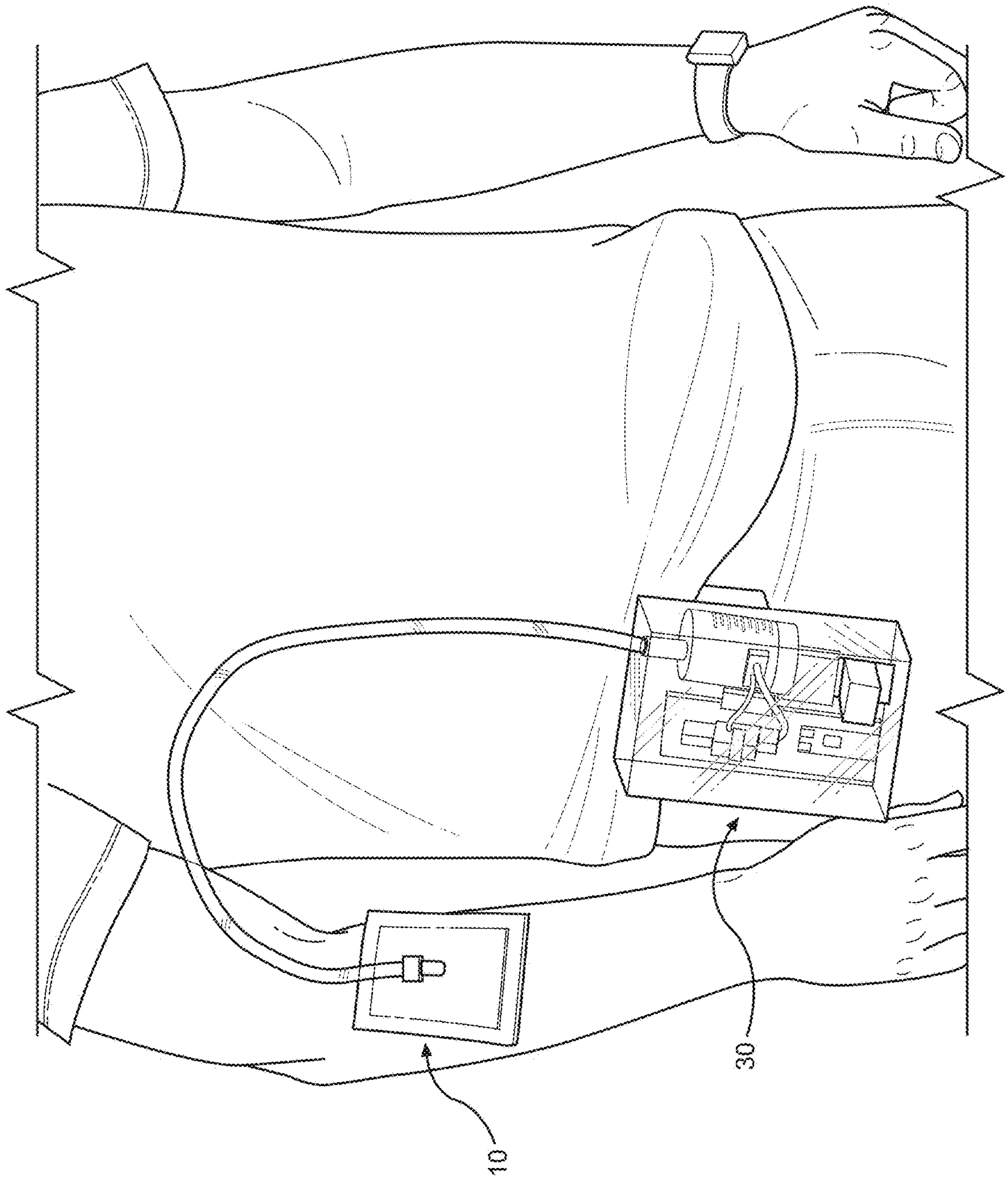

The micro-blower 38 was mounted at one end of the sealed chamber 40 such that, when running, it created a constant flow within the chamber 40, blowing ozonized air at a constant rate through the outlet into the patch 10. Both the ozone generator 32 and micro-blower fan 38 included driver boards 33 and 39, respectively, which were stored in a portable housing (FIG. 1C) along with a battery pack 36 and control circuit 34. The assembled unit 30 can be worn by a user (FIG. 1C) with the housing containing all of the necessary generation components and the patch 10 attached to the user with a medical tape or adhesive such as Tegaderm® waterproof transparent dressing by 3M Company.

In addition to using ozone therapy as a stand-alone treatment, the apparatus may be used for combination ozone and antibiotic treatments to improve the performance of both therapies significantly. The ozone causes damage to an outer membrane of bacterial cells, allowing for increased diffusion of antibiotics into the cells, even in cases where the cells were previously resistant to diffusion therein and in which the antibiotics were ineffective. Ozone achieves this by oxidizing the cell membrane and thereby creating holes for the antibiotic to pass therethrough into an interior of the cell. Because of a reduction of the outer membrane defenses, which is the main differentiation between Gram-positive (G+ve) and Gram-negative (G−ve) strains, it was predicted that the adjunct ozone therapy may enable G+ve antibiotics to affect G−ve strains of bacteria. Using ozone to bypass intrinsic or developed antibiotic resistances of G−ve bacteria may enable the prolonged use of current antibiotic technologies. The combined therapy may also enable reduced application time and dosages relative to use of the antibiotics or the ozone individually, therefore reducing the likelihood of negative health effects of high-concentration ozone exposure and potentially slowing the rate of new antibiotic resistances being developed.

Therefore, in accordance with another embodiment, the patch 10 may further include a dissolvable coating 22 thereon comprising a releasable antibiotic payload. The dissolvable coating 22 is configured to dissolve or degrade upon contact with certain biological materials (e.g., fluids present at the wound site) or in the presence of ozone. In this instance, the dissolvable coating 22 is configured to dissolve upon contact with human skin 24, sweat thereon, and/or a wound thereof. As such, in this embodiment the apparatus is configured to simultaneously apply both gaseous ozone and antibiotics to the wound. Exemplary but nonlimiting materials for the dissolvable coating 22 include water soluble polymers including but not limited to polyvinyl alcohol (PVA) nanofibers. Such dissolvable coating 22 may be a single use, low cost, biocompatible devices suitable for topical deliver of both antibiotic and ozone simultaneously.

The dissolvable coating 22 may include various antibiotics including antibiotics commonly used to treat bacteria resistant to or unresponsive to other antibiotics. Nonlimiting examples of antibiotics may include ceftaroline, ceftazidime/avibactum, ceftolozane/tazobactam, clindamycin, colistin, daptomycin, delafloxacin, doxycycline, imipenem/cilastatin, linezolid, minocycline, omadacycline, oritavancin, polymyxin B, sulfamethoxazole, tedizolid, telavancin, trimethoprim, and vancomycin. The antibiotics may be included individually, in combination with other antibiotics, and/or in combination with other compounds that affect the efficacy of the antibiotics such as certain inhibitors. The antibiotics may be included in the dissolvable coating 22 in various amounts based on their solubility or other relevant factors, and preferably are included in doses sufficient to provide a therapeutic response.

Figure 2A:
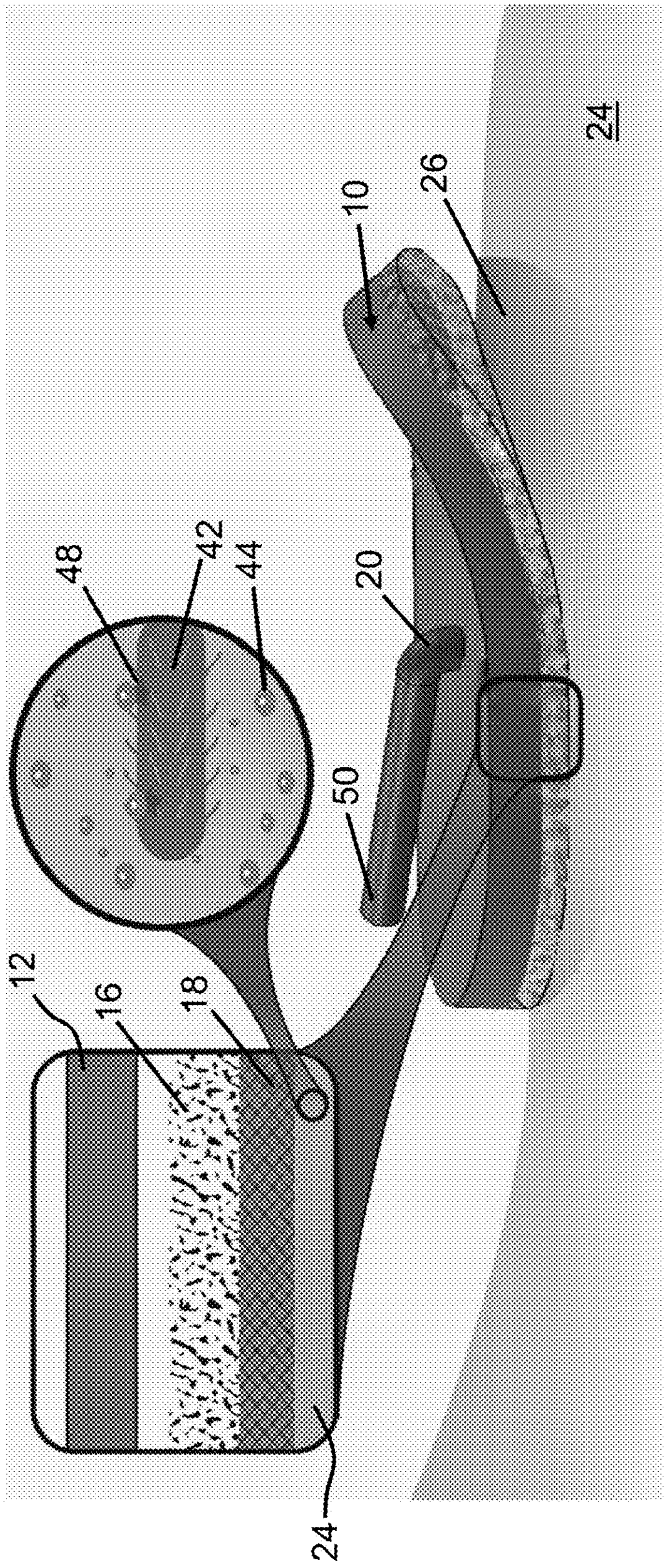
FIGS. 2A and 2B represent a dermal wound with bacteria being treated with applied ozone treatment patches. The ozone delivered to the wound eliminates the microbes through oxidation of the cell wall alone (FIG. 2A) or in combination with application of antibiotics (FIG. 2B). Multiple layers of material create a pore size "gradient" to increase the uniformity of output flow from the patch.
Figure 2B:
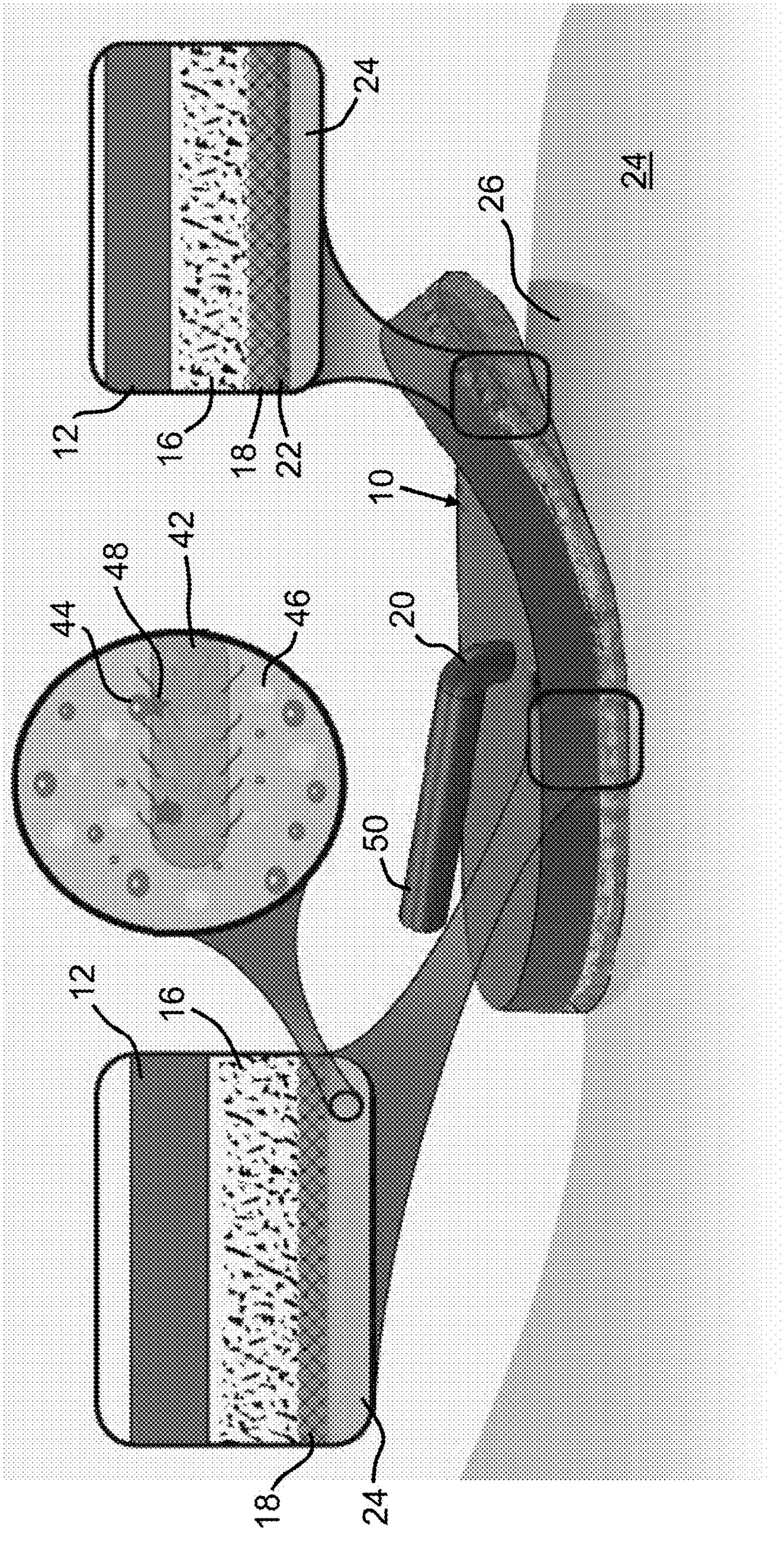

FIGS. 2A and 2B represent nonlimiting methods of treating wounds with the apparatus. In these figures, the ozone generating unit 30 and portions of the tube 50 have been omitted for clarity.

FIG. 2A represents a method of treating a wound site 26 with the patch 10 without the dissolvable coating 22. As represented, the wound contact layer 18 may be placed in direct contact with the wound site 26 of the user or adjacent the wound site 26 for treatment thereof. During treatment, the ozone 44 may be produced with the ozone generating unit 30, provided through the tubing 50 into the patch 10, through the flow dispersion layer 16, and through the wound contact layer 18 toward the wound site 26. The inserts of FIG. 2A schematically represent the presence of the ozone 44 adjacent the wound site 26 and the effect of the ozone 44 on a bacterium cell 42 located thereon. Specifically, the circular insert represents the ozone 44 as causing ruptures 48 in the bacterium cell 42 due to oxidation.

FIG. 2B represents a method of treating the wound site 26 with the patch 10 including the dissolvable coating 22. Similar to the method of FIG. 2A, the wound contact layer 18 may be placed in direct contact with the wound site 26 of the user or adjacent the wound site 26 for treatment thereof. During treatment, the ozone 44 may be produced with the ozone generating unit 30, provided through the tubing 50 into the patch 10, through the flow dispersion layer 16, and through the wound contact layer 18 toward the wound site 26. Concurrently, the dissolvable coating 22 breaks down and releases the antibiotic payload topically to the wound site 26. The rectangular right and left inserts represent the layers of the patch 10 prior to wound contact (right insert) and after wound contact and after the dissolvable coating 22 has dissolved (left insert). The circular middle insert schematically represents the combination therapy of ozone 44 and antibiotics 46 affecting the bacterium cell 42 (middle insert). Specifically, the ozone 44 causes ruptures 48 in the bacterium cell due to oxidation while the antibiotic 46 diffuses into the cell 42.

Nonlimiting embodiments of the invention will now be described in reference to experimental investigations leading up to the invention. For these investigations, both components of the ozone-generation unit 30 and the patch 10 were fabricated using rapid prototype techniques that can be simply adapted to standard scalable manufacturing technologies currently used in production of wound dressings. The ozone generating unit 30 included a small commercial ozone generator (Murata model MHM500), a piezoelectric micro-blower (Murata MZB1001T02), and respective manufacturer's driver circuits. These components, along with a battery and microcontroller circuit were arranged inside a 135 mm×90 mm×70 mm acrylic housing.

The wound contact layer 18 of the patch 10 was fabricated from a 95% Rayon/15% Spandex knit fabric with a PDMS coating applied to an exterior surface thereof. The PDMS coating was prepared by first mixing PDMS elastomers and curing agent at a 1:10 weight ratio, and then diluting with heptane at a volume ratio of 1:5. Prior to application of the PDMS coating, the entire exterior surface of the knit fabric was pretreated and exposed to a plasma treatment in order to increase the bonding of the PDMS coating therewith. The knit fabric was then submerged in the diluted PDMS solution and set in a 70° C. oven to dry for approximately one hour.

The flexible backing 12 was also fabricated from PDMS which was fabricated by mixing the same 1:10 ratio of elastomers to curing agent and pouring the mixture into a mold created for the backing 12. The backing 12 was shaped to match the desired structure of the patch 10, with a centrally located through-hole in for the addition of the gas input connection 20 for coupling with the tubing 50. The mold was then left in a vacuum chamber for one hour before being placed in the oven to cure. Before attaching the wound contact layer 18, a piece of low-density fiber mesh (⅛ in thick polyester batting), used as the intermediate flow dispersion layer 16, was cut to size and inserted into a cavity of the backing 12. To attach the backing 12 to the wound contact layer 18, a double-sided adhesive tape (3M 300LSE) was applied between the backing 12 and an interior surface of the wound contact layer 18 after each surface was plasma treated to increase bond strength. Once the wound contact layer 18 and the backing 12 were secured to one another with the tape, they were both cured in the oven. Once bonded, a connection with the ozone generating unit 30 was made via a 5 mm inner diameter tubing (tubing 50).

The hydrophobicity of the patch 10 was evaluated by measuring the contact angle of water droplets on the Rayon-Spandex knit fabric. An initial measurement was taken of the patch 10 before any treatment, after plasma treatment, and again after PDMS coating. As seen in FIG. 3C, initial contact angle measurements for both the untreated patch 10 and the plasma treated patch 10 were 0°, meaning the droplet was completely absorbed into the material. For the PDMS treated fabric (PDMS-fabric), the contact angle between the patch 10 and the droplet was measured to be between 135° and 150° with super-hydrophobic water repelling properties. The PDMS-fabric showed a superior hydrophobicity as compared to the commercially available polymer film such as Tyvek (CA of 109°).

In order to verify that the PDMS-fabric would remain hydrophobic throughout the use, contact angle measurements were taken over a series of loading cycles. This loading simulated numerous movement cycles of the PDMS-fabric over its lifetime while attached to a user. To implement the loading, the PDMS-fabric was repeatedly exposed to a compressive bending force. In each cycle, the sample was bent with a radius of curvature equal to 13.5 mm. These bending cycles were applied in 25 cycle increments, and the contact angle measurement was taken after each set of 25 cycles, up through 100 cycles. FIG. 3D shows the measured approximate contact angle remained constant throughout the testing cycles.

Figure 3A:
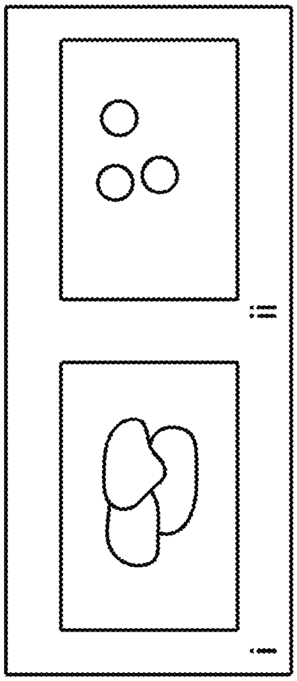
FIGS. 3A through 3D represent hydrophobicity of untreated (I) and PDMS treated (ii) Rayon-Spandex knit fabric sample (FIGS. 3A and 3B), contact angle of the patch surface compared at different steps in the treatment process and Tyvek (FIG. 3C), and contact angle over repeated loading cycles (FIG. 3D). Data is the average of three samples, with error bars indicating standard deviation.
Figure 3B:
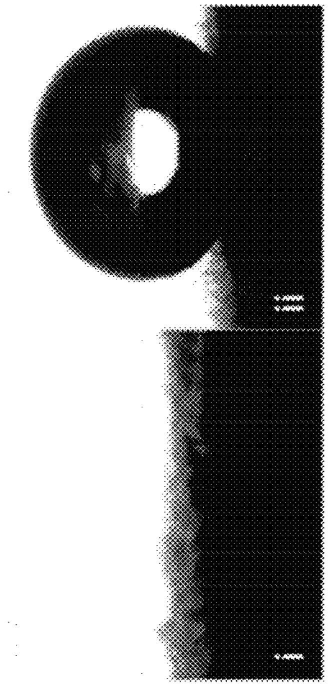
Figure 3C:
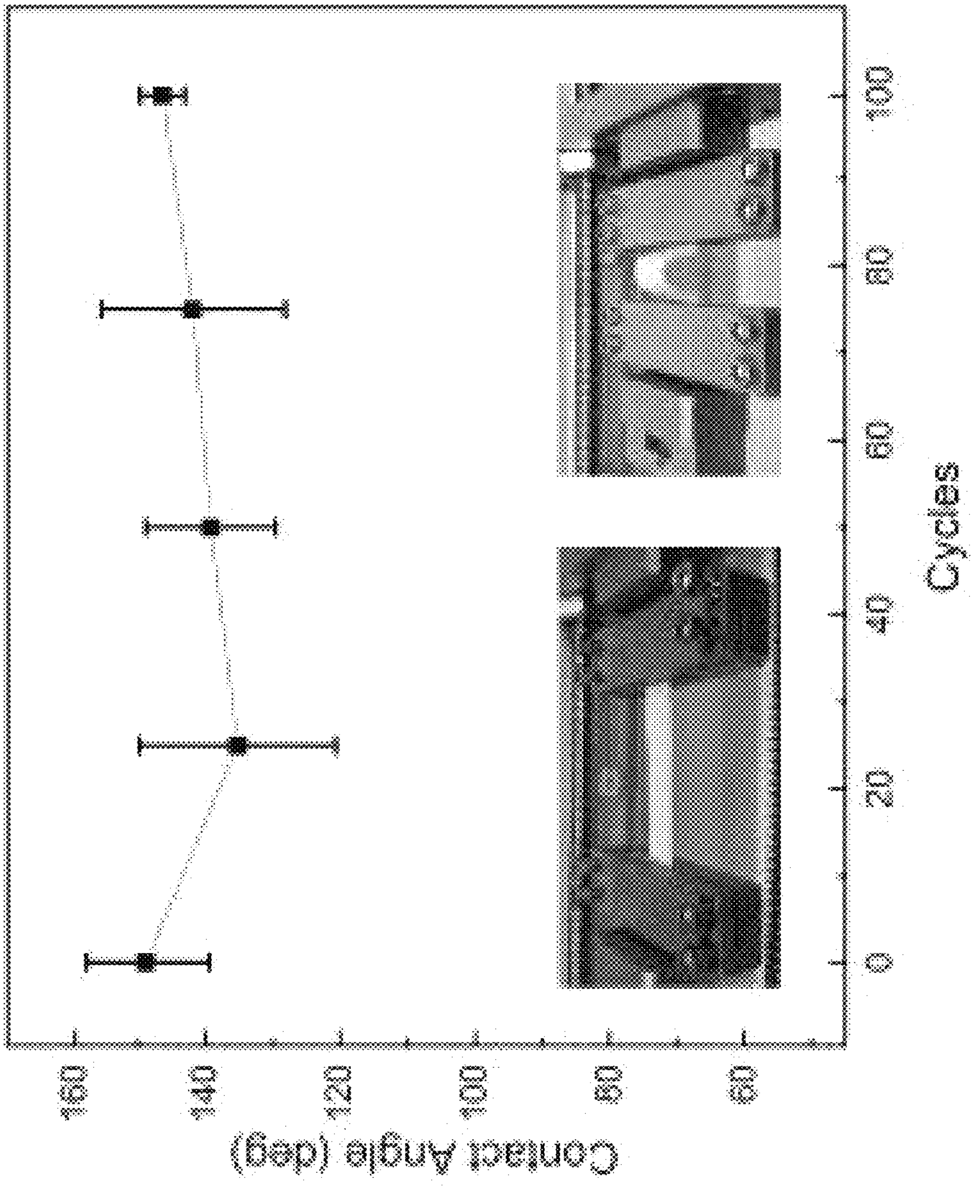
Figure 3D:
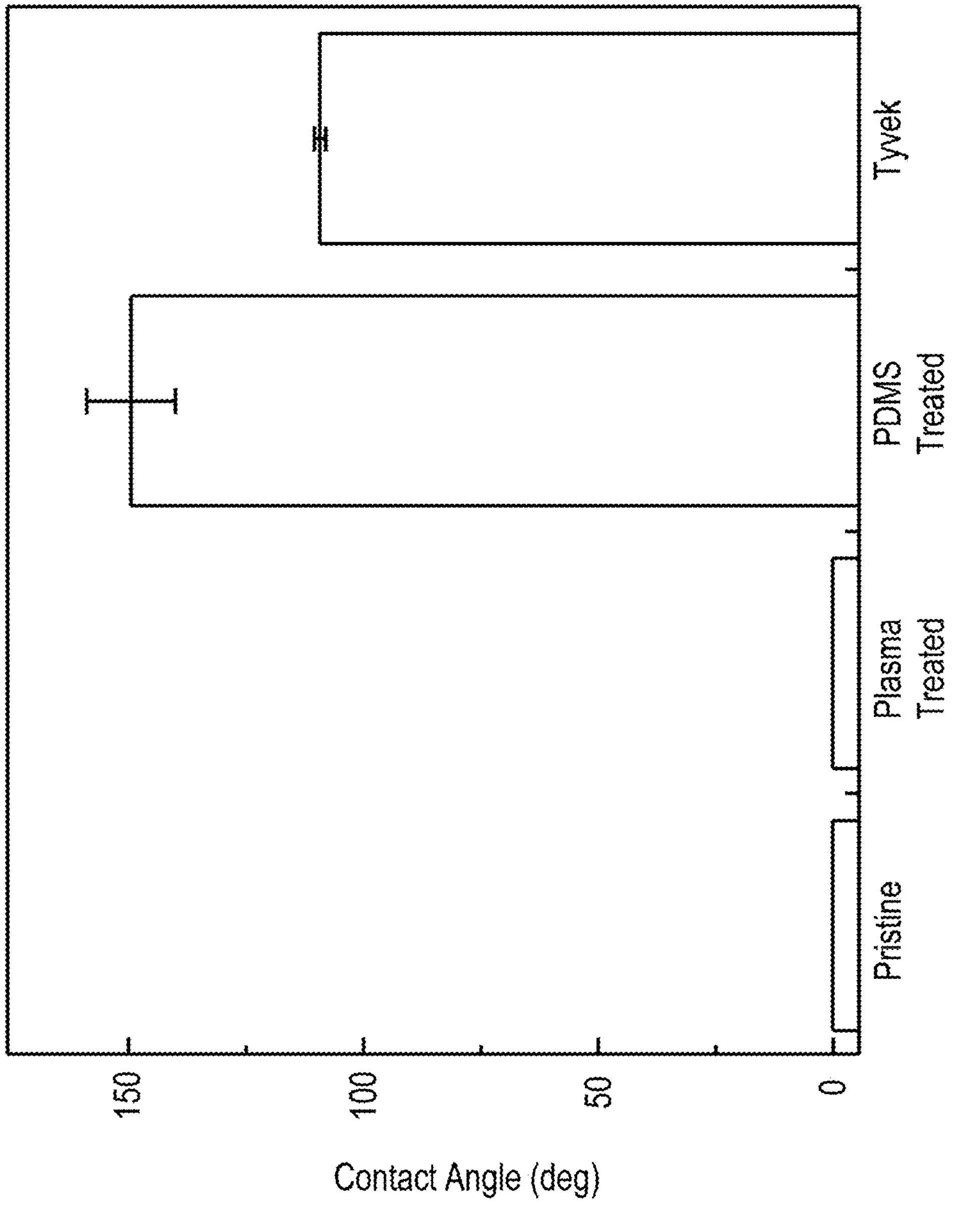

As shown by the initial hydrophobicity results, the PDMS-fabric successfully resisted the water droplets, while the two untreated samples did not (FIG. 3A). The high level of hydrophobicity created by this approach was apparent when the PDMS-fabric contact angle results of 135° to 150° were compared to those of a commercially available hydrophobic, permeable polymer sheet (Tyvek) which has a contact angle of about 109°.

Figure 4A:
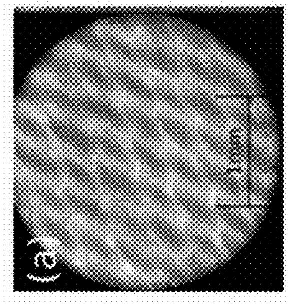
FIGS. 4A through 4B include microscope (FIGS. 4A, 4D, and 4G) and SEM (FIGS. 4B, 4C, 4E, 4F, 4H, and 4I) images of pre-treated Rayon-Spandex (FIGS. 4A-4C), PDMS treated Rayon-Spandex fabric (FIGS. 4D-4F), and an intermediate flow dispersion layer (FIGS. 4G-4I).
Figure 4B:
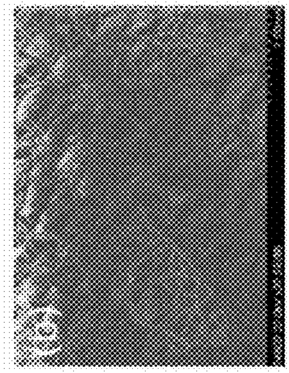
Figure 4C:
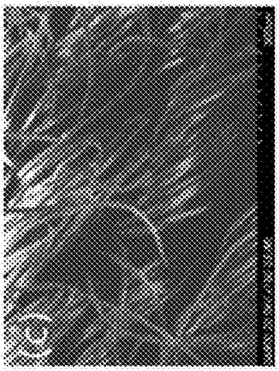
Figure 4D:
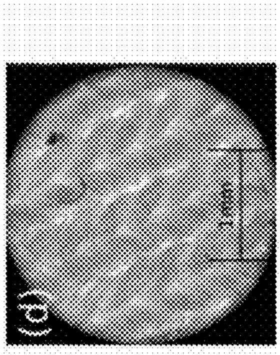
Figure 4E:
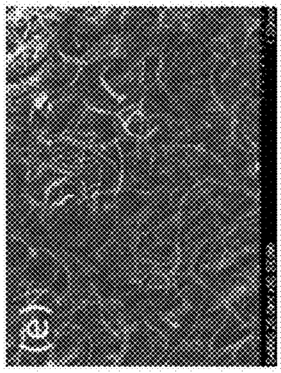
Figure 4F:
Figure 4G:
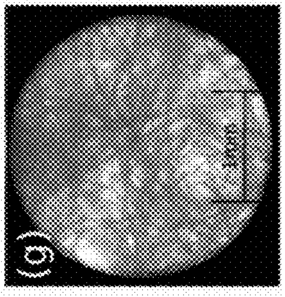
Figure 4H:
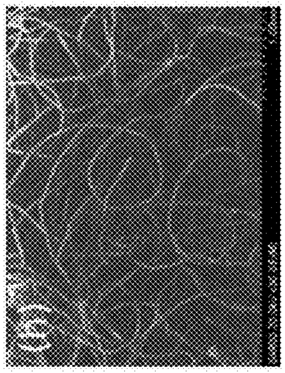
Figure 4I:
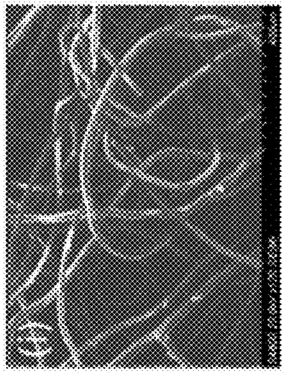

The effects of PDMS treatment on the Rayon-Spandex fabric microstructure and porosity were also investigated. Optical and SEM microscopy were used to analyze the fiber thickness and pore size of the knit fabric before and after PDMS treatment (FIGS. 4A through 4F). As can be seen, the PDMS treatment resulted in a coating of some of the fibers and it is this coating that provided the hydrophobicity observed. The treatment didn't significantly alter the physical structure of the fibers and any change in the porosity due to the PDMS treatment was negligible. Microscopic analysis was also performed on the flow dispersion layer 16 (FIGS. 4G through 4I); the larger and randomly orientated fibers helped distribute the ozone gas more uniformly throughout the patch 10. The dispersion layer 16 had larger pore size distribution (0.003-0.02 $mm^2$) as compared to the wound contact layer 18 (0.002-0.008 $mm^2$), creating a pore "gradient" within the patch 10.

Figure 5A:
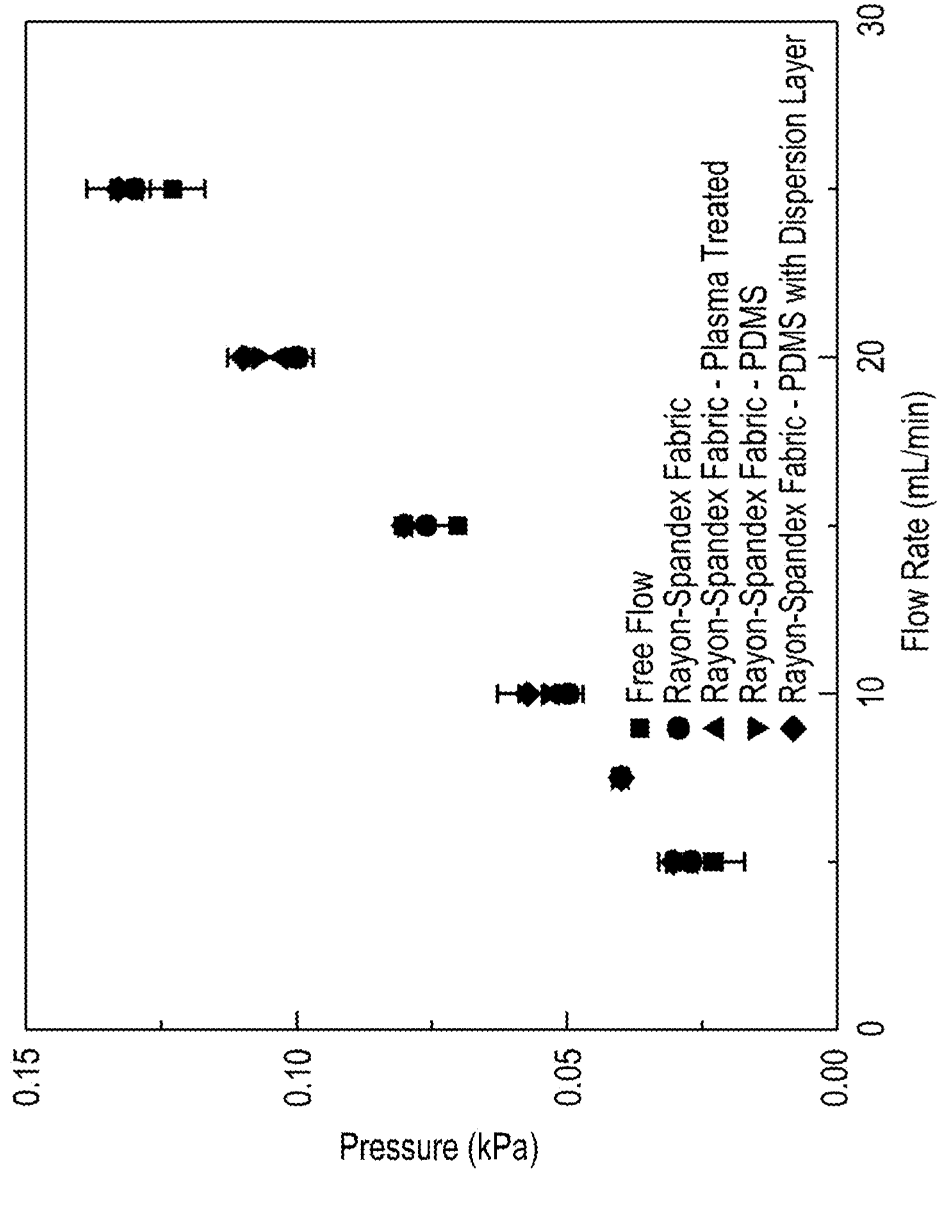
FIGS. 5A and 5B represent permeability characterization of the patch material before and after PDMS coating with and without the dispersion layer, represented by internal pressure from flow resistance measured at different flow rates generated by syringe pump (FIG. 5A), and ozone generation of patch operated with and without a dispersion layer at different flow rates generated by the micro-blower (FIG. 5B). Data is the average of three samples, with error bars indicating standard deviation.

Subsequently, the ozone flow resistance through the knit fabric was quantified. To do this, the internal pressure of the flow was measured at a range of flow rates for the patch 10 at different stages. This indicated how much the PDMS and intermediate dispersion layer 16 impede the delivery of the ozone through the patch 10. FIG. 5A shows the flow resistance characterization of the knit fabric before and after the PDMS coating with and without the intermediate flow dispersion layer 16. As can be seen, the PDMS coating had an insignificant effect on the flow resistance, leading to no increase in the internal pressure at any flow rate. When the flow dispersion layer 16 was added, there was no discernable increase in the flow resistance (the slope without the intermediate layer being 0.0053 kPa $mL^{-1}$ $min^{-1}$, whereas adding it changed the slope to 0.0054 kPa $mL^{-1}$ $min^{-1}$).

Figure 5B:
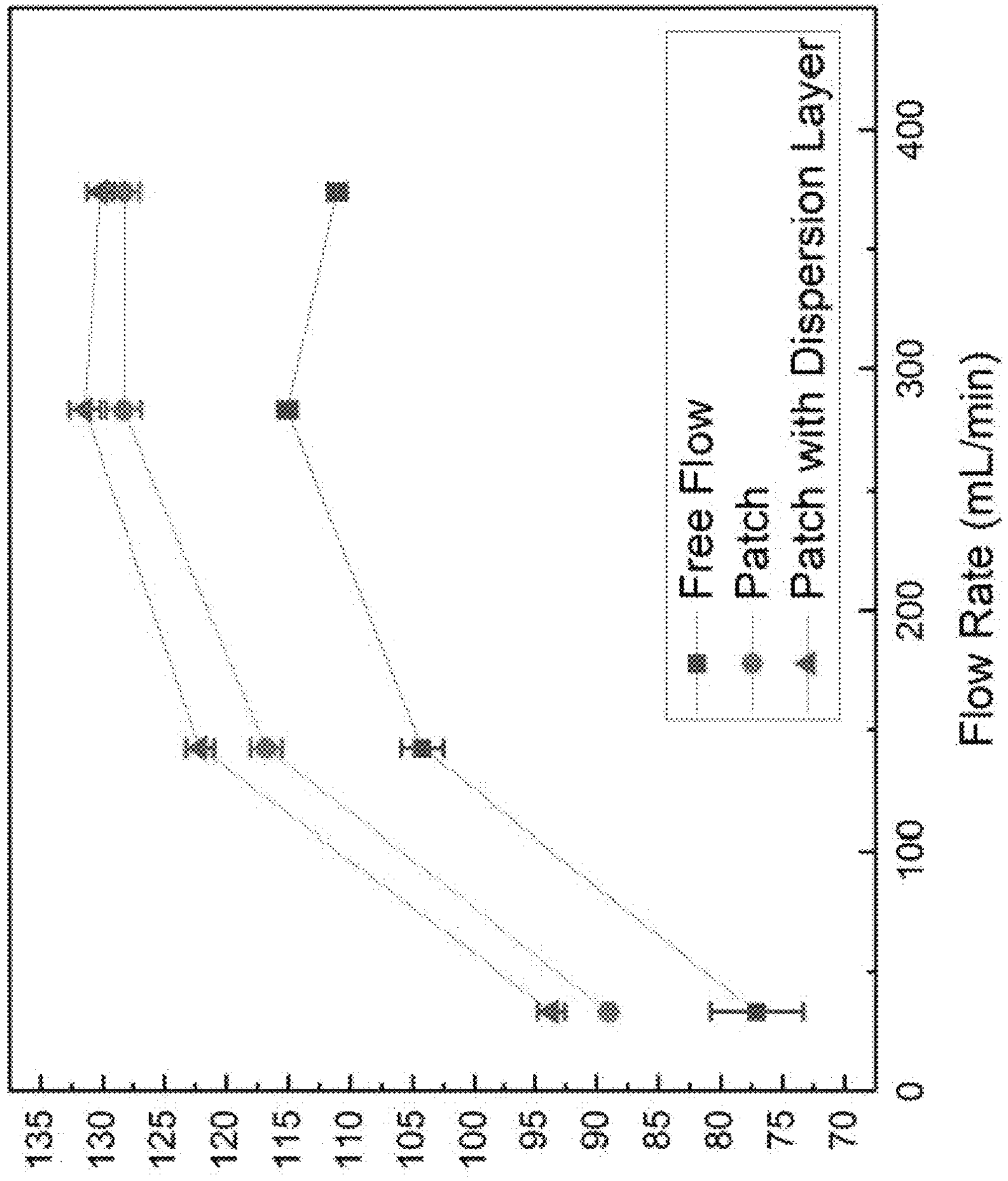

The concentration of ozone delivered through the patch 10 was also characterized. The ozone concentration at the gas output (i.e., the exterior surface of the wound contact layer 18) was measured for four different inputs to the micro-blower 38, each with and without the intermediate flow dispersion layer 16 in the patch 10 and without any knit fabric, while the output from the ozone generator 32 was held at a constant 4 mg $hr^{-1}$ (FIG. 5B). As expected, at low flow rates the micro-blower 38 delivered lower ozone concentrations at the exterior surface (about 90 ppm). Increasing the output of the micro-blower 38 increased the ozone concentration up to 130 ppm after which the concentration started to decrease. The free stream concentrations were lower than those using the patch 10, both with and without the dispersion layer 16 by about 10%. This was likely due to how the ozone generation scheme interacts with the change in flow behavior due to the presence of the patch 10. Ozone was generated a constant mass rate, so the concentration delivered was a function of the flow rate. When the flow dispersion layer 16 was added, the flow was slowed down and spread out. Thus, a slightly higher concentration was measured as the same amount of ozone was contained within a smaller volume of gas (a 1% increase).

Figure 6A:
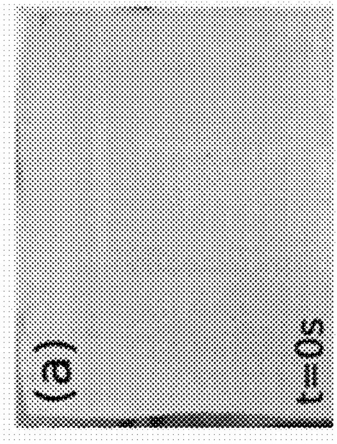
FIGS. 6A through 6E represent ozone detection strip images without an intermediate flow dispersion layer (FIG. 6A before and 6B after) and with an intermediate flow dispersion layer (FIG. 6C before and 6D after), and area measured by detection strip over time (FIG. 6E). Data is the average of three samples, with error bars indicating standard deviation.
Figure 6B:
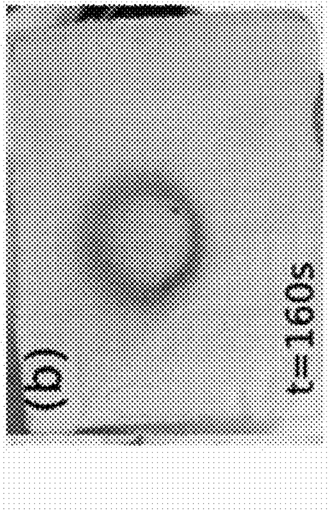
Figure 6C:
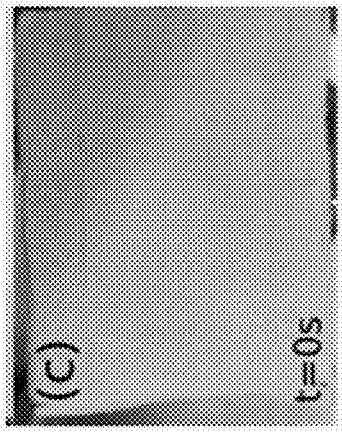
Figure 6D:
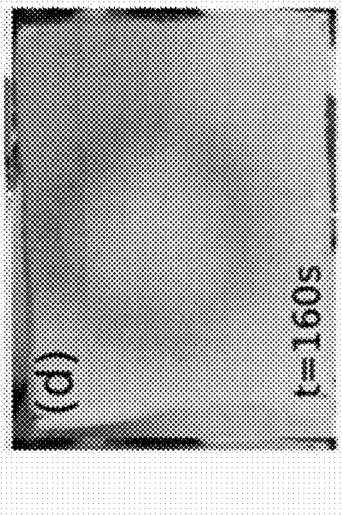
Figure 6E:
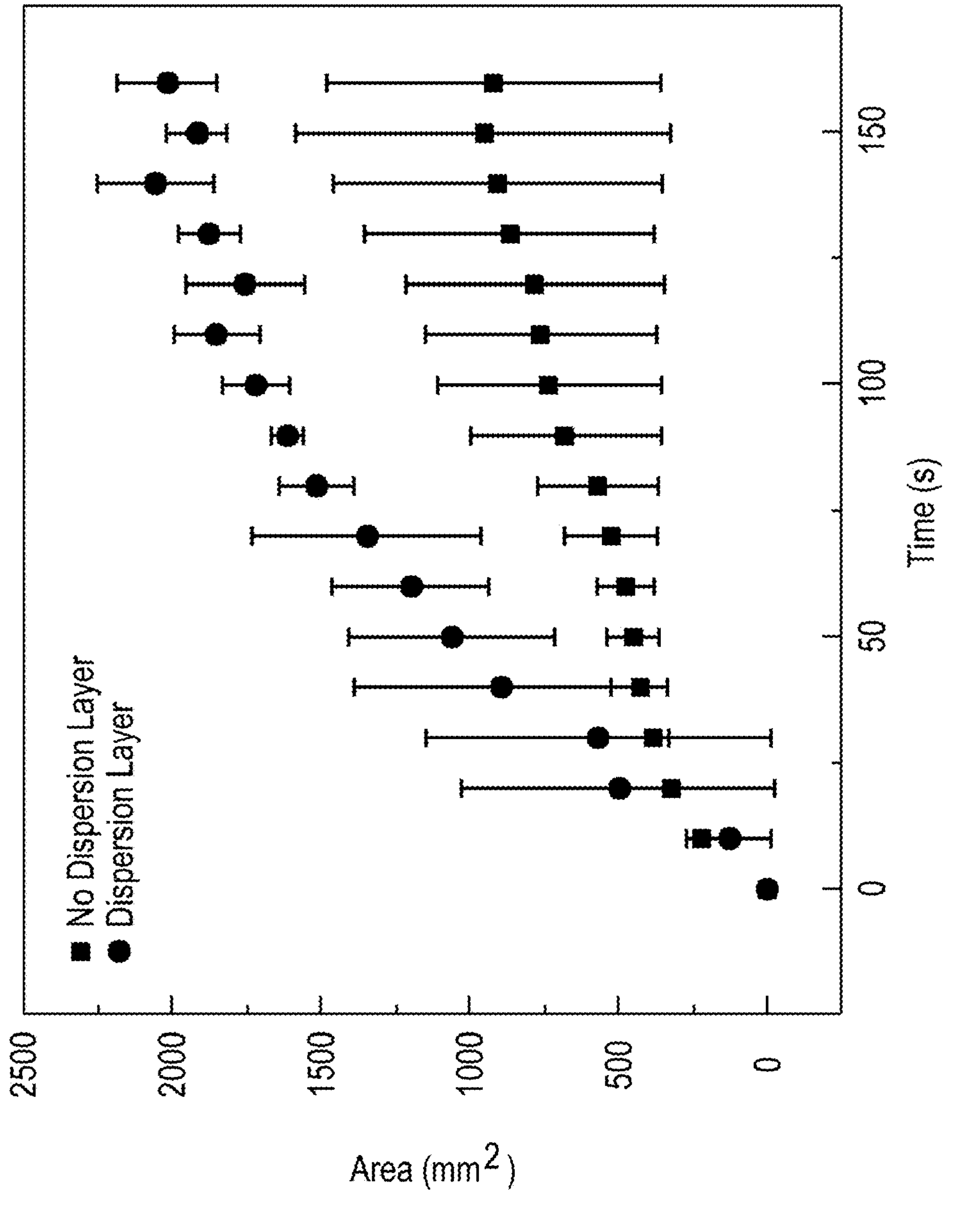

To better characterize the ozone distribution at the exterior surface of the wound contact layer 18, time dependent ozone concentration was mapped using an ozone sensitive test strip. The strip was placed on top of the patch 10 while ozone was forced through and pictures were taken at regular intervals. FIGS. 6A through 6D show the qualitative 2D distributed ozone generated by the patch 10 with and without the intermediate dispersion layer 16. FIG. 6E shows the effective ozone treated area over time with and without the dispersion layer 16. As can be seen in both the images and the graph, the intermediate flow dispersion layer 16 increased the effective treatment area. There was a greater than 250% increase in the total effective treated area detected using the porous intermediate dispersion layer 16 in the patch 10 over 160 seconds.

Figures 7A, 7B, 7C:
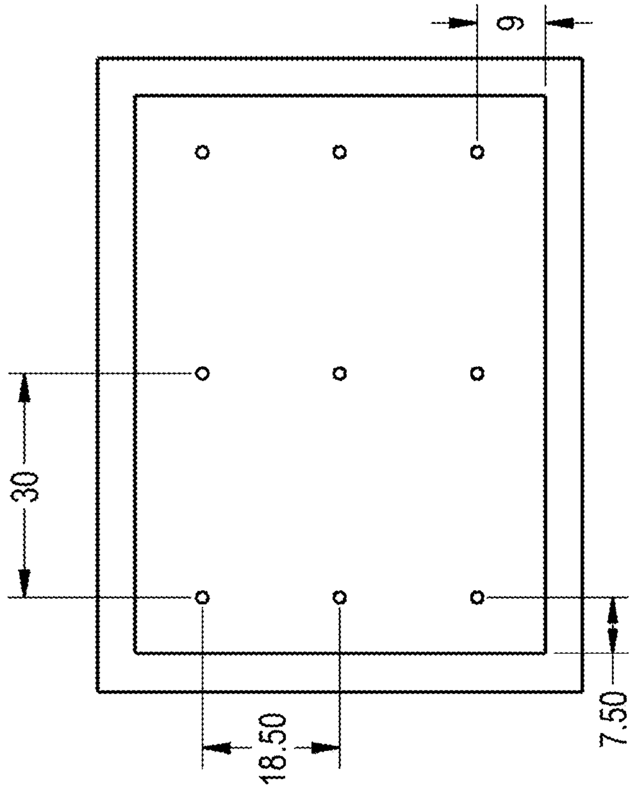
FIGS. 7A through 7C represent ozone distribution detection points on a patch (FIG. 7A) and results of a recorded ozone concentration delivery map (ppm) without and with an intermediate flow dispersion layer (FIGS. 7B and 7C, respectively). Each measurement the average of three data points at location.

The spatial dispersion of the ozone through the patch 10 was also assessed by directly measuring the ozone output levels at nine select points across the patch 10 as shown in FIG. 7A. FIG. 7B shows the recorded ozone concentration levels (ppm) at each location without the intermediate flow dispersion layer 16, and FIG. 7C shows concentration values with the dispersion layer 16. It can be seen that greater concentrations of ozone reached the outer portions of the patch 10 when the intermediate flow dispersion layer 16 was included. This confirms the design provided greater dispersion of ozone across the treatment area.

Figure 8A:
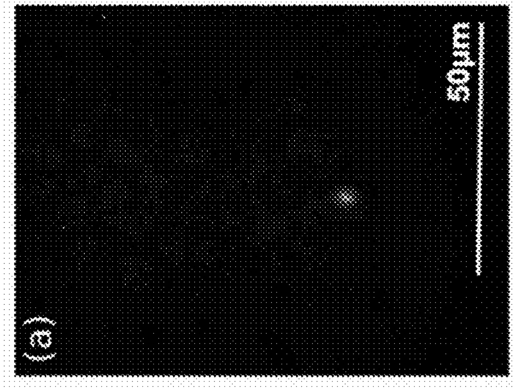
FIGS. 8A through 8H include ozone therapy results for *S. epidermidis*: stain imaging of initial (FIG. 8A), control at six hours (FIG. 8B), and ozone treatment at six hours (FIG. 8C), and *P. aeruginosa*: stain imaging of initial (FIG. 8D), control at six hours (FIG. 8E), and ozone test at six hours (FIG. 8F). *S. epidermidis* concentration graph during ozone treatment (FIG. 8G) and *P. aeruginosa* concentration graph during ozone treatment (FIG. 8H). Data was collected from triplicate samples, with error bars indicating standard deviation.
Figure 8B:
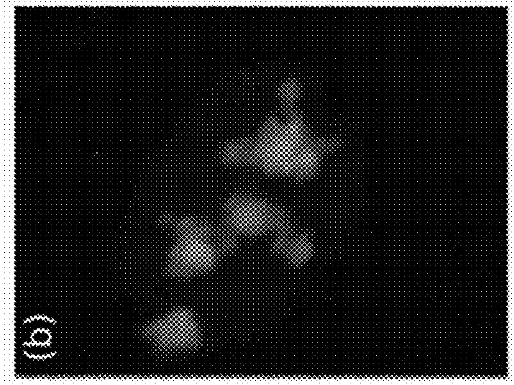
Figure 8C:
Figure 8D:
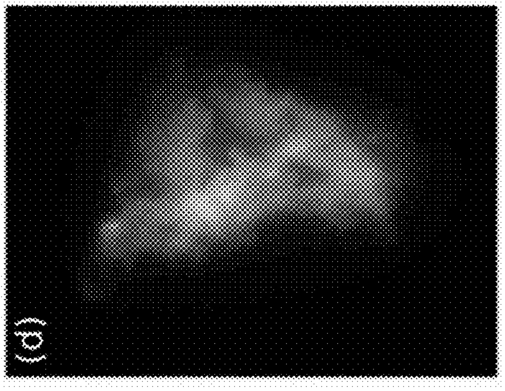
Figure 8E:
Figure 8F:
Figure 8G:
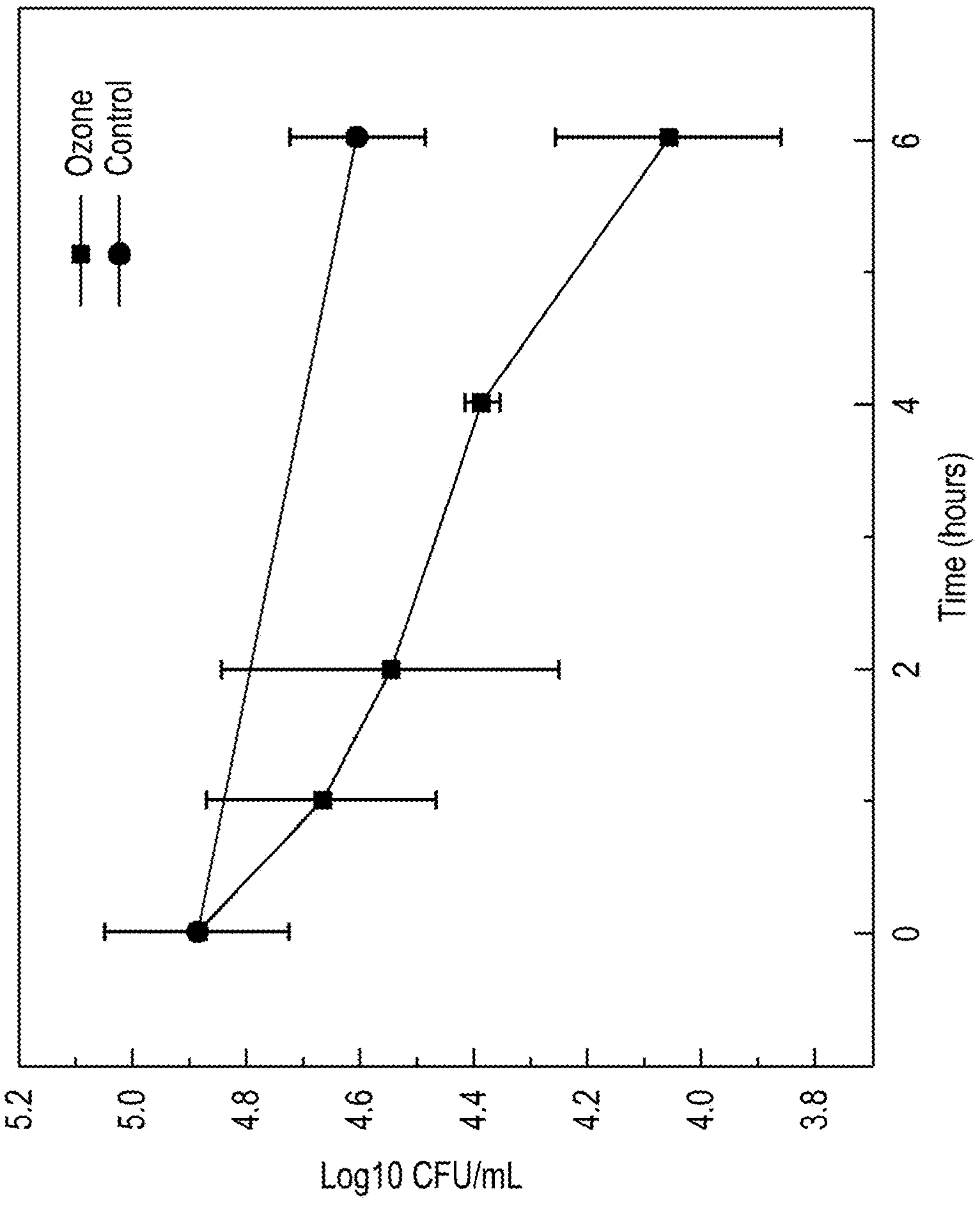
Figure 8H:
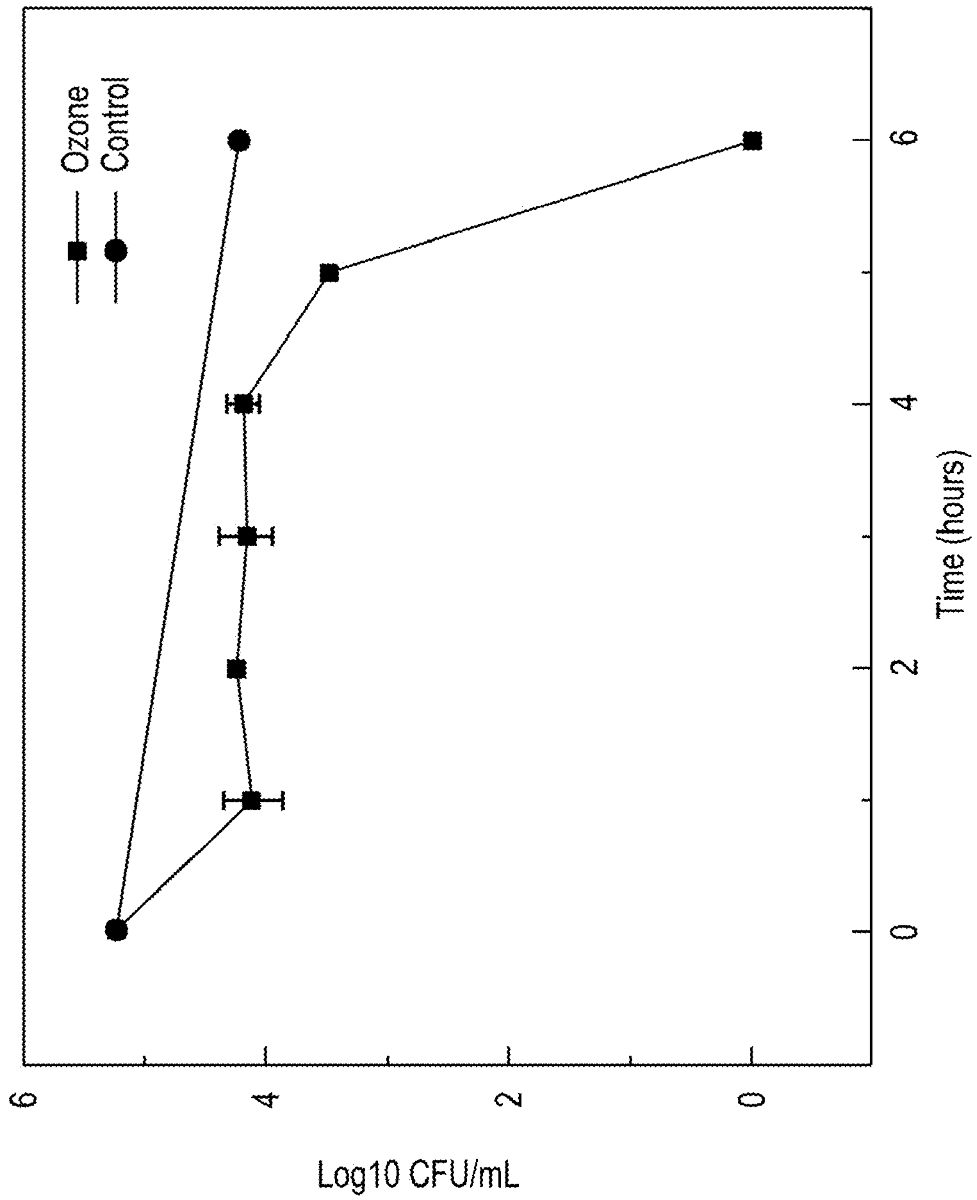

The antibacterial properties of the patch 10 were assessed by exposing multiple strains of antibiotic resistant bacteria (both Gram-negative and Gram-positive) to the ozone applied by the patch 10 for six hours, and measuring the living concentration every one to two hours. Experiments using two common strains of antibiotic resistant bacteria common in skin infections, *S. epidermidis* NRS101 and *P. aeruginosa* ATCC 15442, indicated positive results. Over the course of six hours of exposure, the Gram-positive bacteria *S. epidermidis* showed greater than 70% reduction from the starting inoculum (0.8 $\log_{10}$ reduction CFU/mL) (FIG. 8G). FIGS. 8A through 8C show bacteria stain images of the samples before and after treatment, and a control. At first, all of the bacteria were stained green, and then any dead bacteria were re-stained with the red. These images show qualitatively that the bacteria before the treatment are living, and afterward are mostly dead. These results indicate that a single ozone treatment/exposure can be used to eliminate a substantial portion of the present bacteria. Additionally, results for the Gram-negative bacteria, *P. aeruginosa*, indicated even better results. When tested in the same conditions, the apparatus was able to completely eradicate the initial 5 log CFU/mL concentration of *P. aeruginosa* within the six hours of treatment, while the control population was again relatively unchanged (FIG. 8H). FIGS. 8D, 8E, and 8F show similar stain images for *P. aeruginosa.*

The results of typical antibiotics on *P. aeruginosa* and *S. epidermidis* are well known. In both cases, there are antibiotics that are known to be effective (for example, colistin and meropenem for *P. aeruginosa* and rifampicin and vancomycin for *S. epidermidis*), as well as those which are resisted (for example, penicillin and tobramycin for *P. aeruginosa* and penicillin and oxacillin for *S. epidermidis*). As such, these results, for both Gram-positive and Gram-negative bacteria, indicate that ozone treatment can be an effective solution for antibiotic resistant bacteria strains.

Figure 9A:
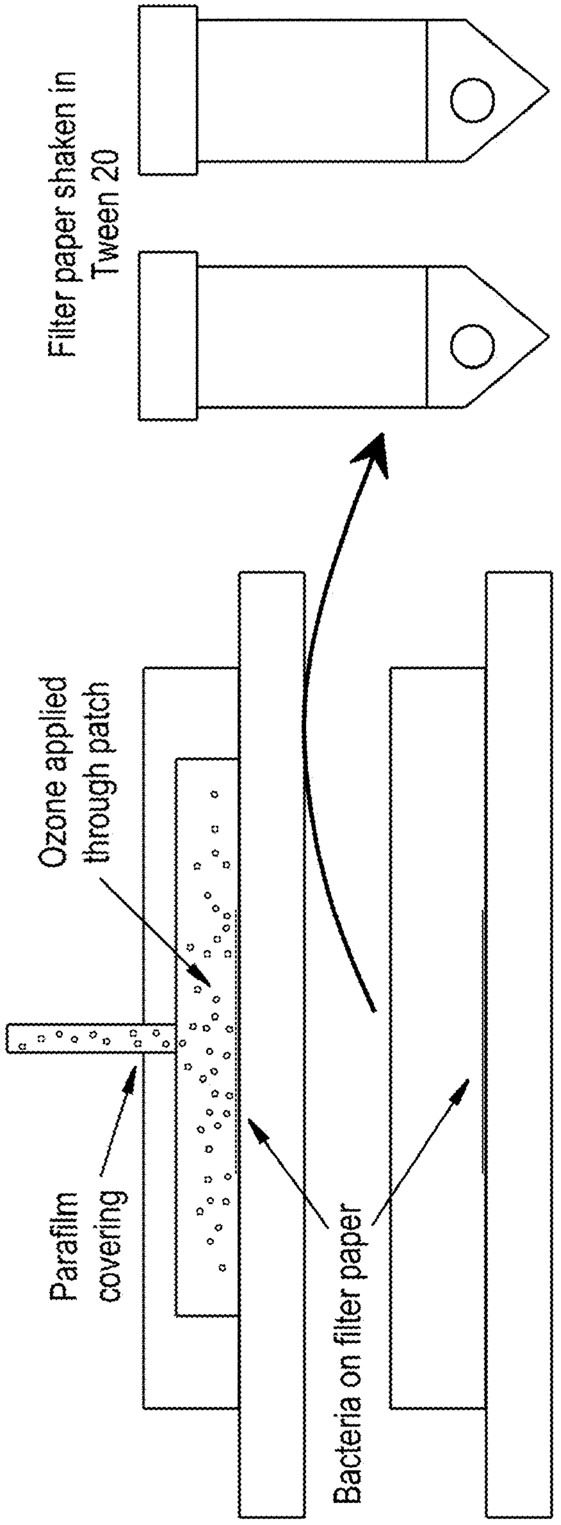
FIGS. 9A and 9B represent a diagram of an experimental setup used for testing the effect of prolonged patch exposure to biofluid (FIG. 9A) and antimicrobial results of pristine patch and pretreated patch in contact treatment of *P. aeruginosa* over six hours (FIG. 9B). Error bars indicate standard deviation.
Figure 9B:
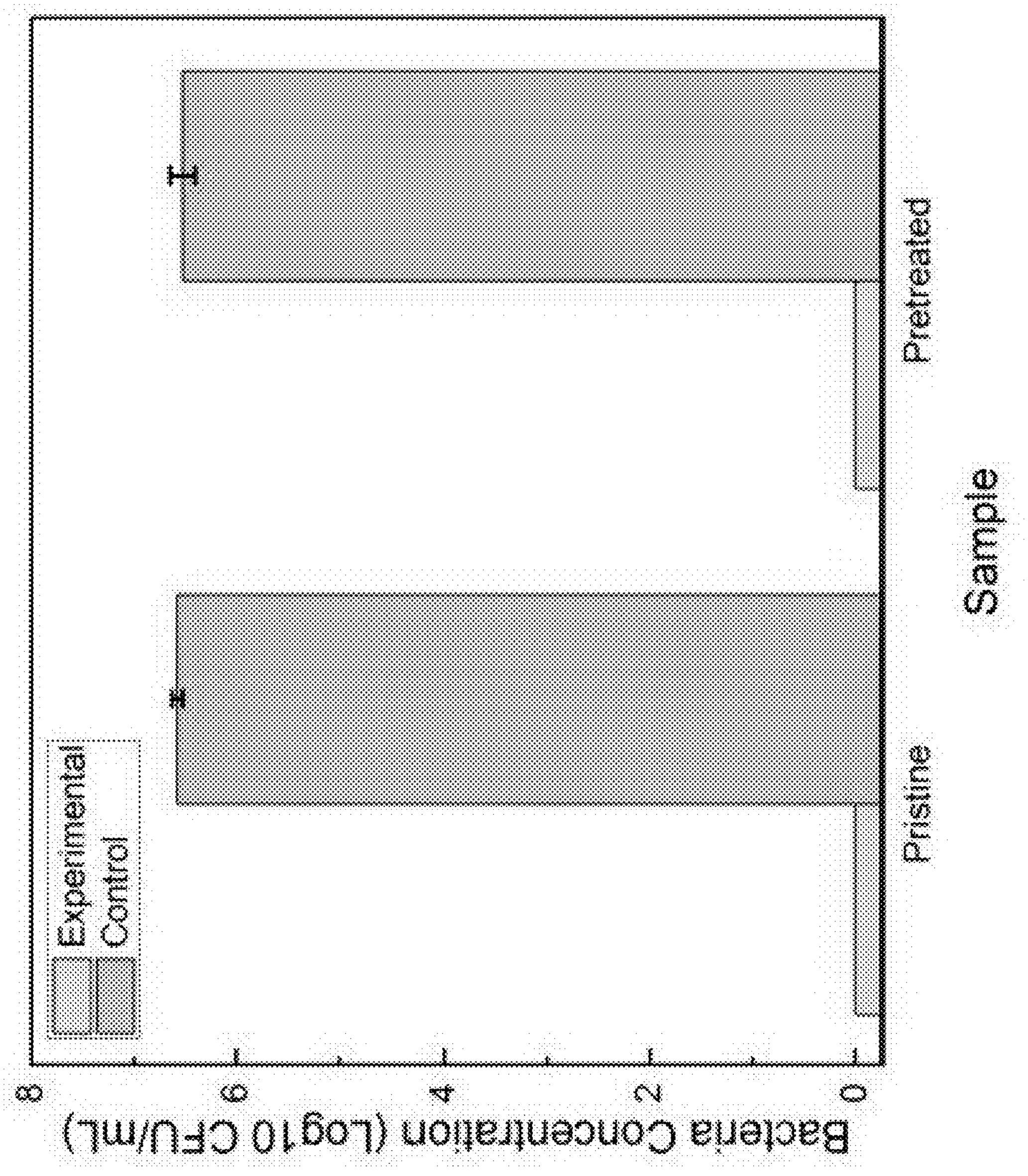

A secondary study was also conducted on *P. aeruginosa* to verify that prolonged contact to a wound environment would not change antimicrobial properties. In each case, 100 μL of *P. aeruginosa* was diluted into 1 mL of PBS and spotted onto filter paper. Each experimental trial was exposed to the ozone for six hours. The first test was conducted through an untreated patch 10, while the second was conducted using a patch 10 that had been preconditioned by resting on a damp sponge filled with mammalian cell culture media overnight. FIGS. 9A and 9B report the results of the tests when compared to the controls, which were prepared in the same way, but exposed to no ozone treatment. In each case, the ozone treatment showed a complete elimination of bacteria. The difference in total concentrations is a factor of variations in starting inoculum and growth time, but the consistent proportional kill-off indicates that the preconditioning of the patch 10 had no significant effect on the antimicrobial results.

Figure 10A:
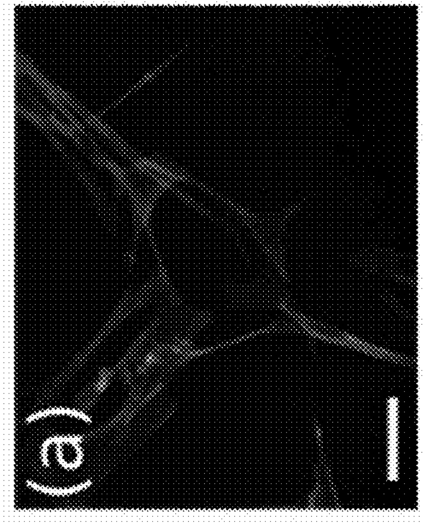
FIGS. 10A through 10D include images of normal mammary fibroblasts HMS-32 cells initial (FIG. 10A), after six hours of ozone treatment (FIG. 10B), 24 hours after ozone treatment (FIG. 10C), and 48 hours after ozone treatment (FIG. 10D). Scale bar 10 micrometers.
Figure 10B:
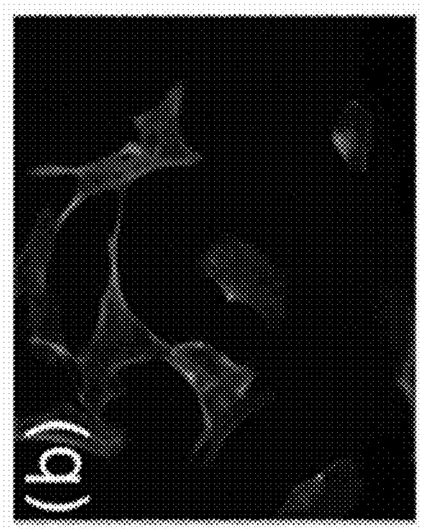
Figure 10C:
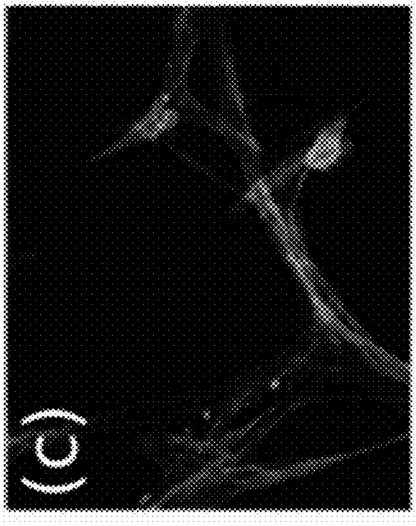
Figure 10D:
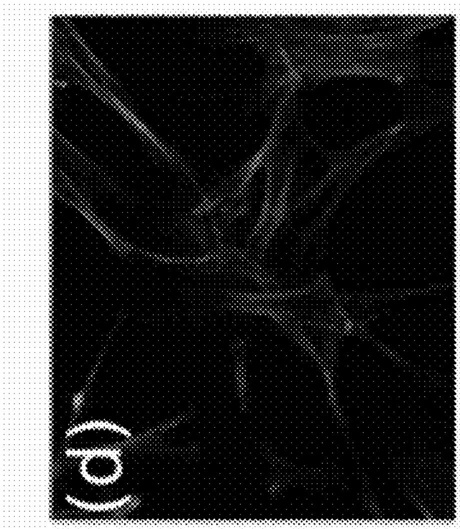
Figure 10E:
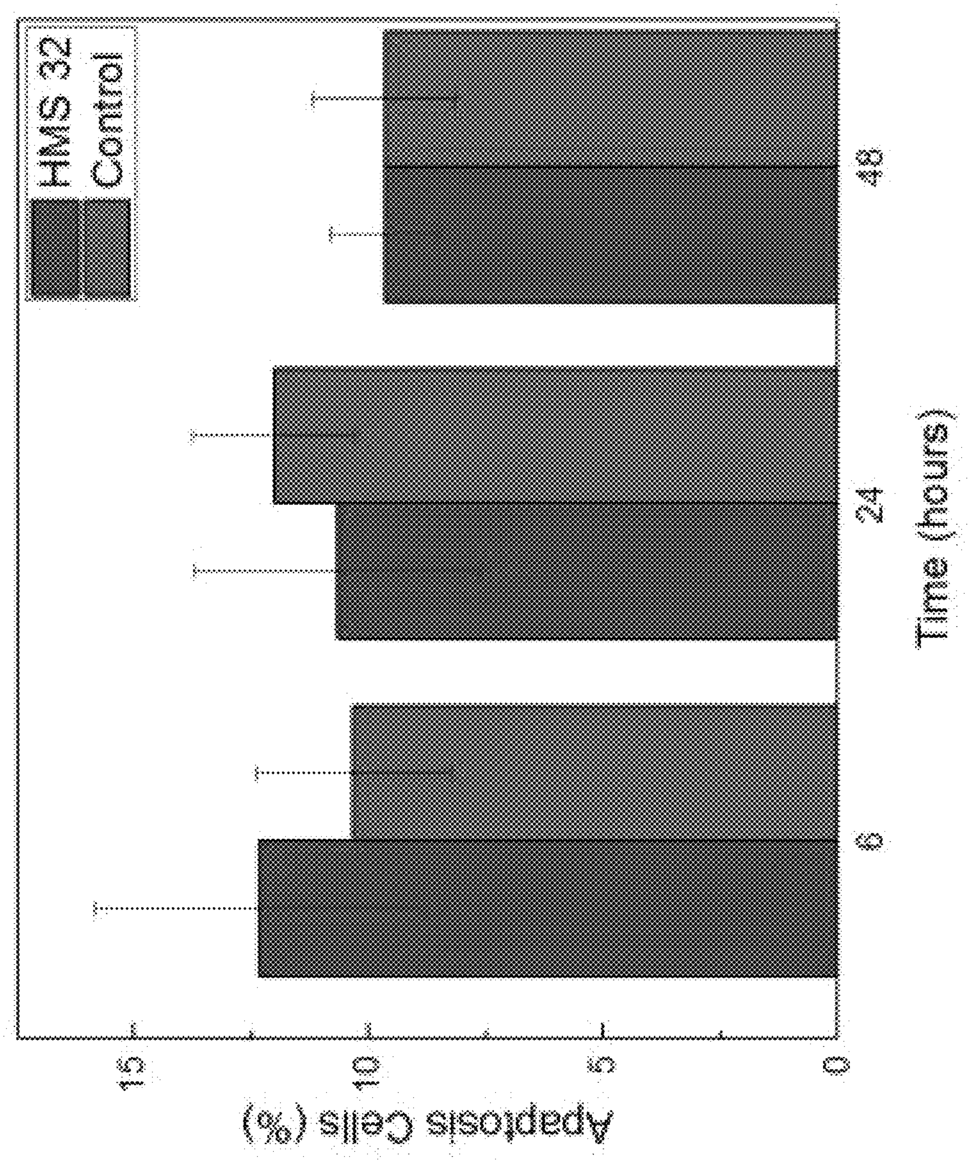
FIG. 10E contains a graph showing percentage of apoptotic cells at each time in a control group and an experimental group. Data was collected from triplicate samples, with error bars indicating standard deviation.
Figure 11A:
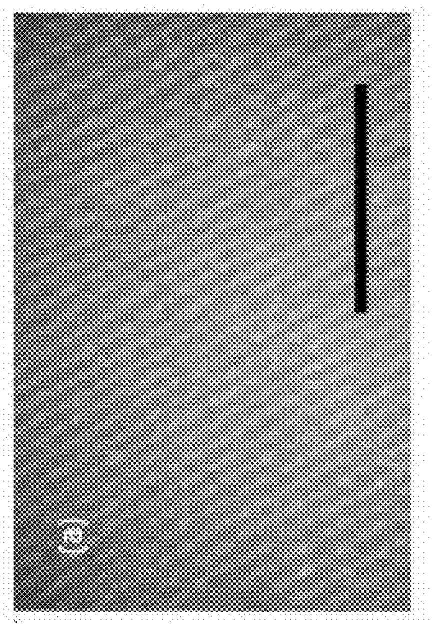
FIGS. 11A through 11H represent images having various magnifications of the wound contact layer prior to depositing the nanofibers (FIGS. 11A and 11B), after depositing nanofiber comprising linezolid (FIGS. 11C and 11D), after depositing nanofiber comprising vancomycin (FIGS. 11E and 11F), and after dissolution of the nanofibers (FIGS. 11G and 11H). Scale bars are 500 micrometers for FIGS. 11A, 11C, 11E, and 11G; 50 micrometers for FIGS. 11B and 11H; and 10 micrometers for FIGS. 11D and 11F. Images were acquired using an optical microscope (FIGS. 11A, 11C, 11E, and 11G) and a scanning electron microscope (SEM.
Figure 11B:
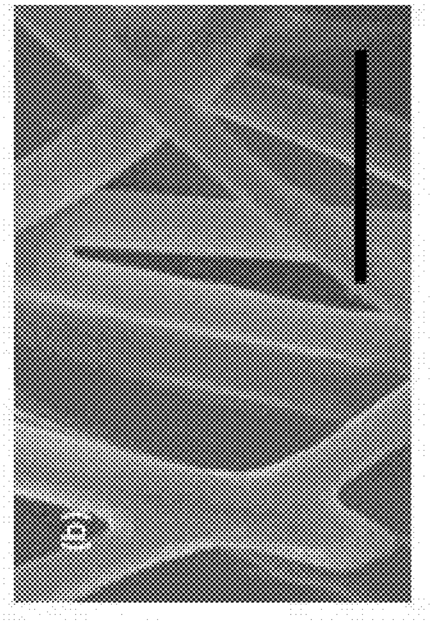
Figure 11C:
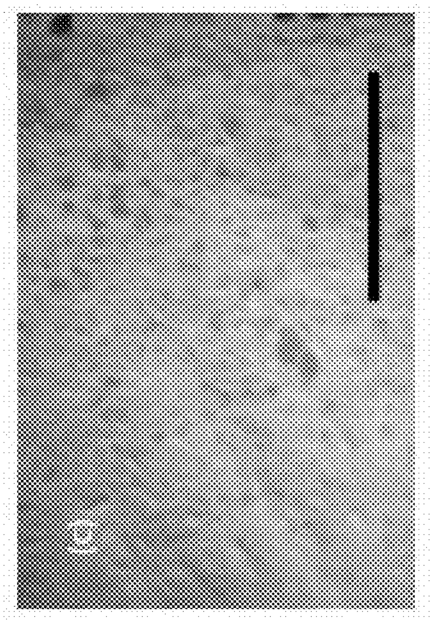
Figure 11D:
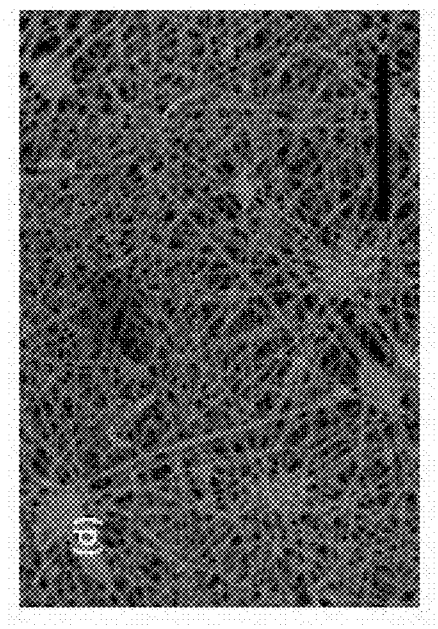
Figure 11E:
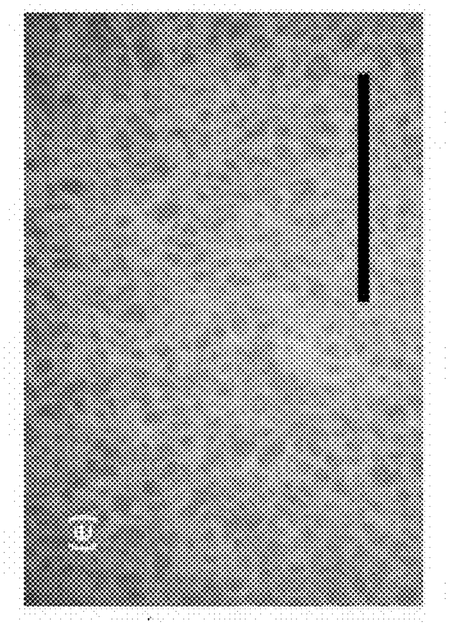
Figure 11F:
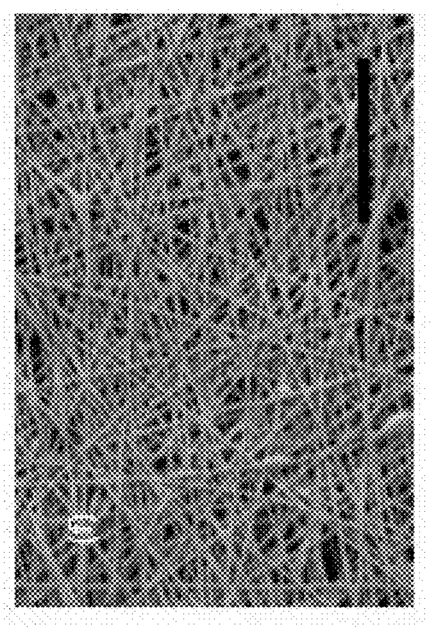
Figure 11G:
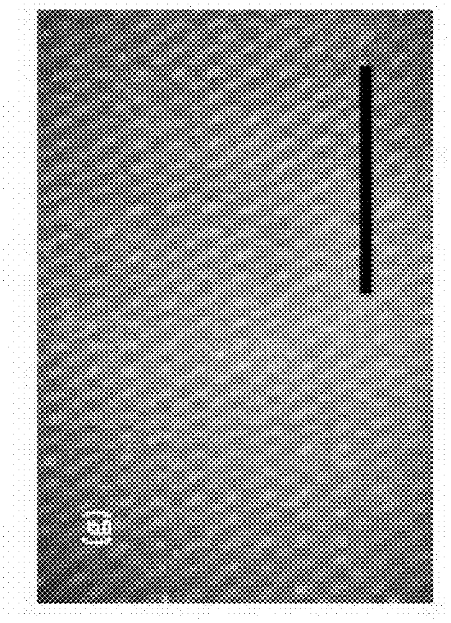
Figure 11H:
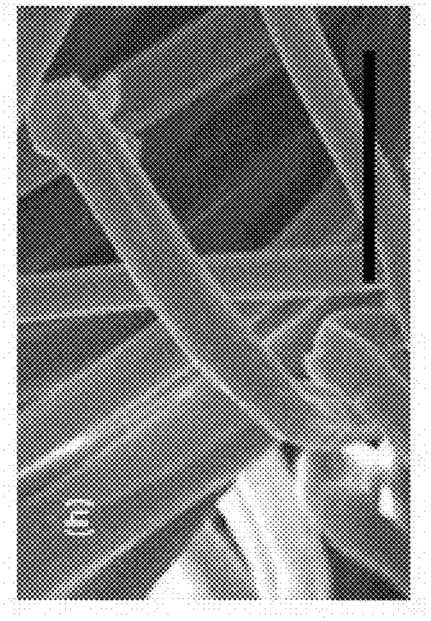

The possibility for the use of ozone to treat antibiotic resistant infections is also dependent on the apparatus not damaging the normal skin cells. Cytotoxic experimentation was conducted to determine how the ozone treatment would interact with human skin cells (FIG. 10A through 10D). Contact effects of the patch 10 were not directly included in the biocompatibility test because both Rayon-spandex fabric and PDMS have been shown to be biocompatible. Ozone treatment has been used to increase the healing process for chronic wounds, so there is good reason to believe a high level of biocompatibility exists. FIG. 10E shows the number of viable cells observed after six hours of ozone exposure, which was the similar duration of exposure used for bacteria. It also shows results 24 hours and 48 hours after treatment to determine if ozone treatment caused any detrimental effect on the cells over time. It can be seen that there was no significant increase in cell apaptosis cells after six, 24, and 48 hours (6.5% over 48 hours). Similar to the stain imaging done for the antimicrobial results, FIGS. 10A through 10D are stain images that show the health of the cells at each time point. In each cell, F-actin was stained green, and the nuclei were stained blue. These images support finding minimal cytotoxicity because there is no noticeable difference in the images over time. At the applied dosage, it can be concluded that ozone, as a treatment method, produces no negative effects on the healthy human cells it contacts.

The antimicrobial properties of ozone delivered through the patch 10 seemed to be effective in reducing or eliminating bacteria that often cause antibiotic resistant wound infections. The concentrations of ozone delivered topically (90-130 ppm), while still larger than the allowed EPA concentrations, are still confined to the wound area and much easier to contain or filter for safe application. Ozone therapy may work synergistically with traditional antibiotic treatments when used in a combination therapy. One of the mechanisms of bacterial resistance against antibiotics is development of changes in cell membrane and hence preventing entrance of antibiotic into the cell. By oxidizing the outer layer of the bacteria, ozone could eliminate this barrier and allow the antibiotics to enter the bacterial cell in order to be effective. Finally, ozone exposure over a given time can accelerate the wound healing by inducing oxidative stress to the cells, stimulating the protective mechanisms of cells and organs, therefore, increasing the efficacy of endogenous oxygen free radicals' scavenging properties as well as enhancing the Krebs cycle production of ATP.

To examine the efficacy of the combination of ozone and antibiotic treatment, the patch 10 was fabricated as described above, but with the dissolvable coating 22 comprising a layer of nanofibers deposited on an exterior surface of the wound contact layer 18. Specifically, nanofibers were electrospun from a polyvinyl alcohol (PVA) and water solution (10% w/w PVA). Antibiotics were added to the nanofibers according to their solubility: 0.03% w/w for Linezolid and 0.1% w/w for Vancomycin. To generate the nanofiber layer, the wound contact layer 18 was adhered to a drum of an electrospinning machine and operated to deposit the nanofibers thereon. The nanofibers were spun from a needle using an 18 g tip with 20 kV and −2 kV potential and 0.65 mL/min flow rate. For the investigations disclosed herein, the nanofibers were deposited until an antibiotic concentration of 20 g/cm$^2$ was reached.

Imaging was performed on the contact wound layer 18 to analyze the size and structure of the nanofibers that were generated through the electrospinning process. FIGS. 11A through 11H show the imaging results from both an optical microscope (OM) and a scanning electron microscope (SEM).

Image comparison of the PDMS treated contact wound layer 18 before and after application and dissolution of the nanofibers indicated that there was little to no change to the structure caused by deposition and dissolution of the nanofibers. This property was further confirmed and quantified in characterizations discussed below. Viewing the images of the nanofibers deposited on the contact wound layer 18, it could be concluded that the mesh generated was again of a porous structure. The average fiber size was approximated to be about 300 nm in diameter for the nanofibers containing vancomycin and about 100 nm in diameter for the fibers containing linezolid. This difference in size was expected to be caused by the larger molecular size of vancomycin (1449.3 Da for vancomycin compared to 337.3 Da for linezolid).

To further characterize the properties of the wound contact layer 18 comprising the dissolvable coating 22, two performance parameters were verified. First, the contact angle of the sample was measured before, with, and after deposition of the nanofibers. The contact angle of the sample corresponds to the hydrophobicity. This property reduces the likelihood of uptake of biofluids into the wound contact layer 18, which could inhibit the flow of the ozone treatment. As described previously, hydrophobic properties were instilled into the wound contact layer 18 through the diluted PDMS coating deposited thereon.

Figure 12:
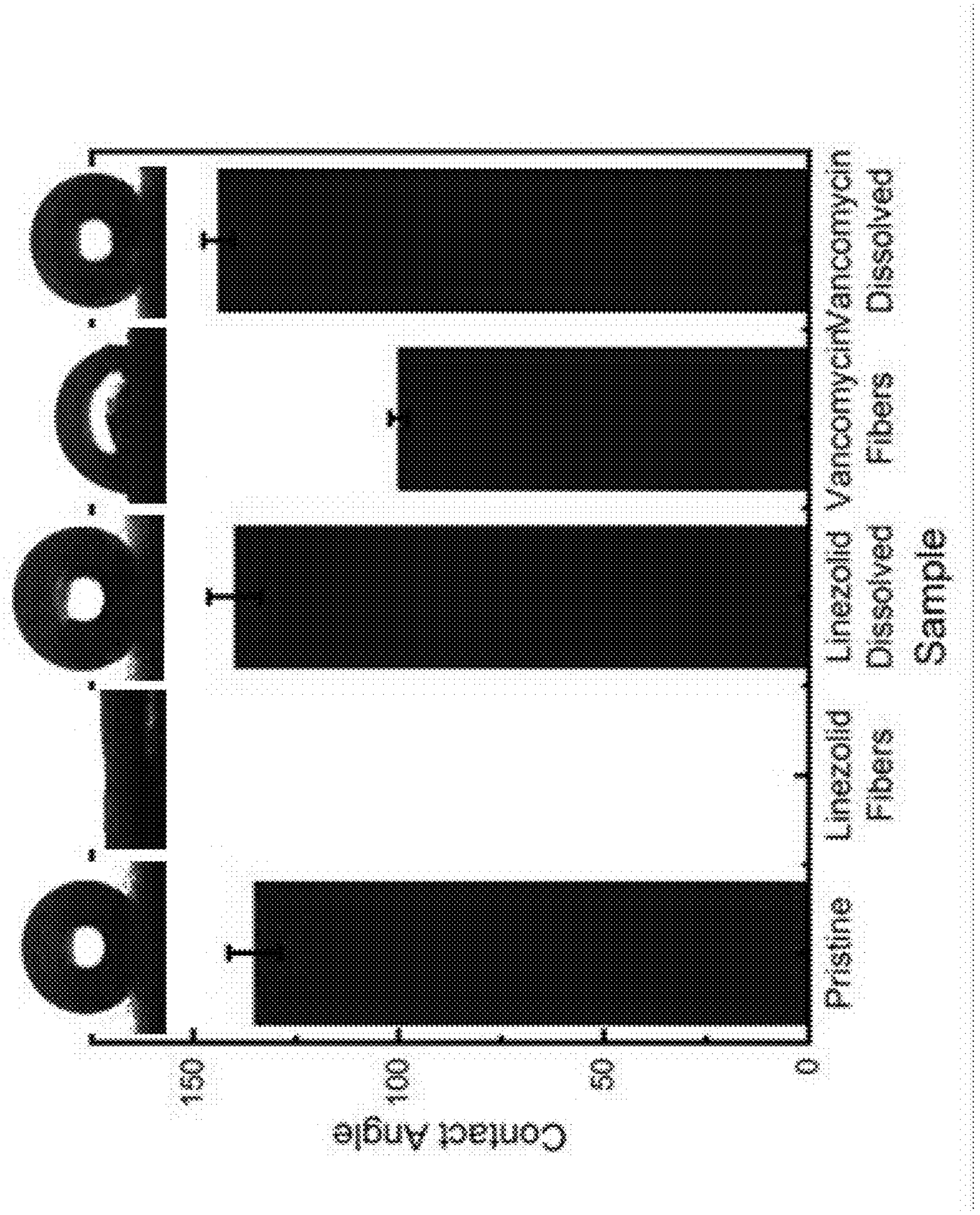
FIG. 12 represents contact angle measurements of the wound contact layer at various stages of treatment.

The results indicated that the hydrophobic behavior of the wound contact layer 18 has little or no change after the nanofibers have been deposited and then dissolved (FIG. 12). This shows that the desired hydrophobicity was maintained throughout the course of the treatment time. It can also be seen that the addition of the dissolvable layer on the wound contact layer 18 temporarily increased the hydrophilicity of the patch 10. This was because the outermost layer of the PVA nanofibers was hydrophilic. This was beneficial because it incited the interaction of biofluid and drug-eluding nanofibers to speed up the dissolution process as will be discussed hereinafter.

A secondary property related to the overall performance of the treatment was the porosity of the dressing with and without the dissolvable coating 22. The porosity of the wound contact layer 18 allows the gaseous ozone to permeate and topically affect the wound area. This property was quantified by measuring the internal flow pressure as a constant flow rate was pumped through the wound contact layer 18. The state of the wound contact layer 18 was varied to characterize this at different times in the treatment process.

Figure 13A:
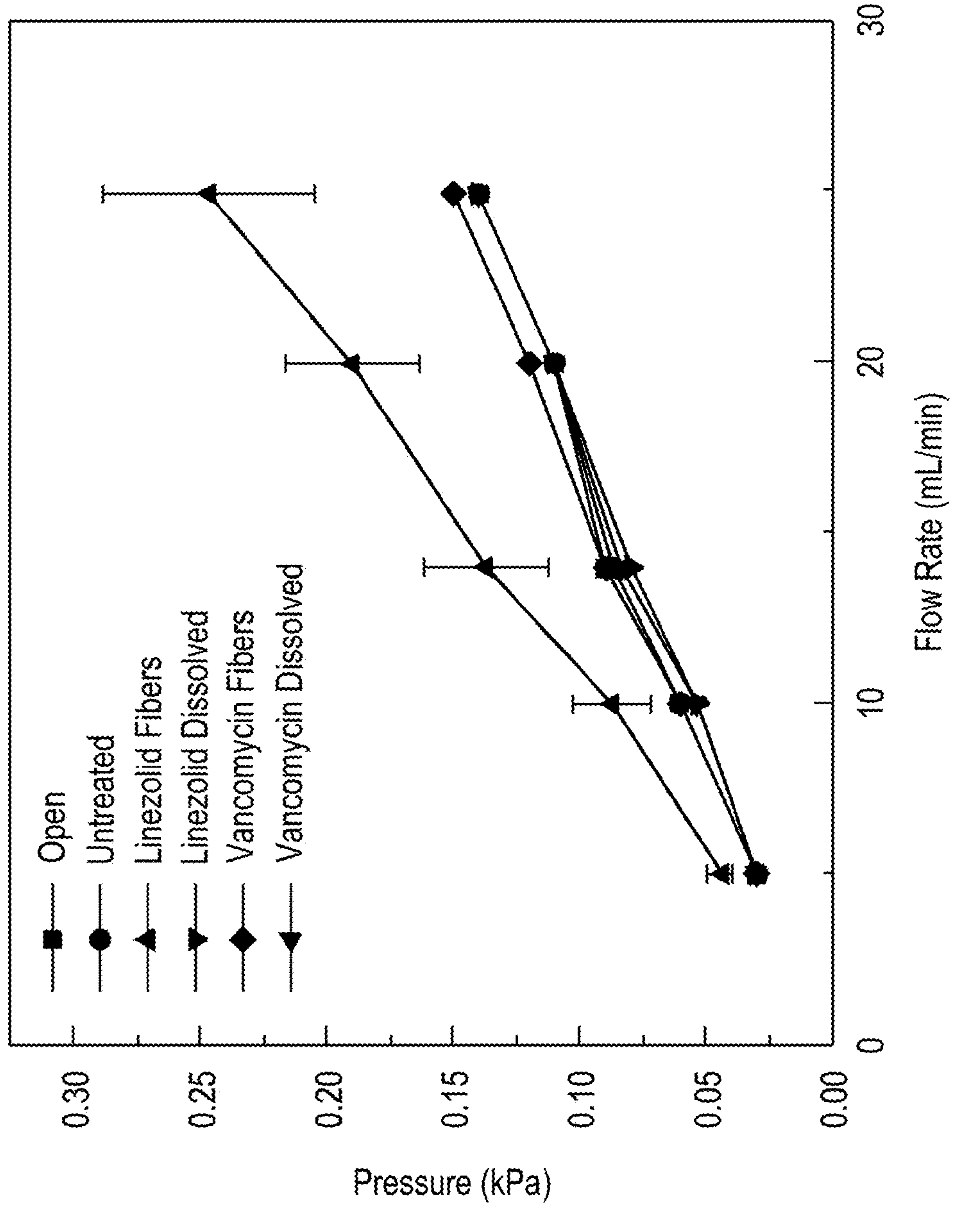
FIGS. 13A and 13B represent internal flow resistance at varying flow rates for the wound contact layer at different stages of application (FIG. 13A), and a comparison of internal flow resistance at 25 mL/min (FIG. 13B).
Figure 13B:
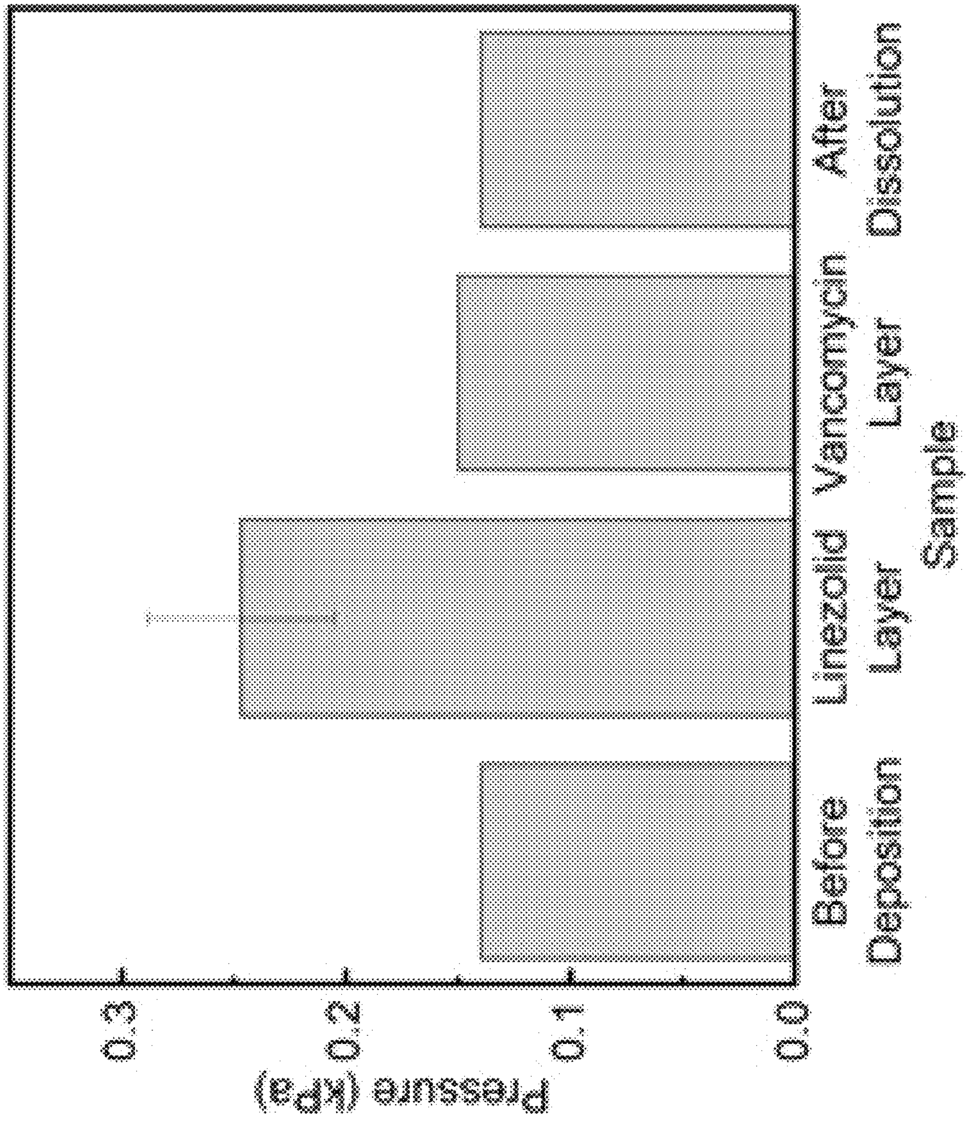

FIG. 13A shows the measured internal pressure at flow rates ranging from 5-25 mL/min. It can be seen that there was no discernable increase in the resistance to flow for any of the samples except for the wound contact layer 18 with deposited linezolid nanofibers thereon. The resistance to flow increased by about 80 percent at the highest flow rate (FIG. 13B). This increase was due to the addition of a significant layer of drug-eluding nanofibers. Because the linezolid fibers were deposited in a much thicker layer (667 g/cm$^2$ vs. 100 g/cm$^2$ for vancomycin), there was a much larger effect on the resistance to gaseous flow. Still, even the increased levels of porosity did not prohibit gaseous flow, as the overall effect was reduced due to the porous mesh structure of the nanofibers as represented in FIGS. 11A through 11H. Due to the fast-dissolving nature of the nanofibers (as seen below), the overall effect of this temporary decrease in porosity was expected to be negligible.

The dissolution rate of the nanofibers into the wound site 26 was quantified. The dissolution time affects the rate at which the active antibiotic is applied to the wound area for treatment and the duration during which the porosity of the dressing is reduced in the case of linezolid nanofibers. To characterize the dissolution time, nanofibers containing a dye with a molecular weight similar to each antibiotic were electrospun under the same conditions. Linezolid containing fibers were dyed with a 319.9 Da methylene blue dye and vancomycin containing fibers were dyed with a 1373.1 Da direct red 80 dye. These dyed nanofibers were then used as models for the dissolution of the drug-eluding nanofibers.

Specifically, the nanofibers were electrospun as previously described onto an aluminum foil substrate attached to the electrospinning drum. All deposition characteristics were kept the same. Samples were cut to size using a laser cutter with a 40 W fiber laser (1.06 micrometers). 0.3 cm$^2$ samples were placed in a 96-well plate and exposed to 300 L of DI water. One set of samples was removed after one minute, and each following sample after an additional two minutes. The solution was then shaken to homogenize and 100 L samples were pipetted into another 96-well plate, and the absorbance was measured with a spectrophotometer. This procedure was replicated for pH variance experiments, with the DI water being replaced by clear buffer solution with pH values of 6, 7, and 8.

Figure 14A:
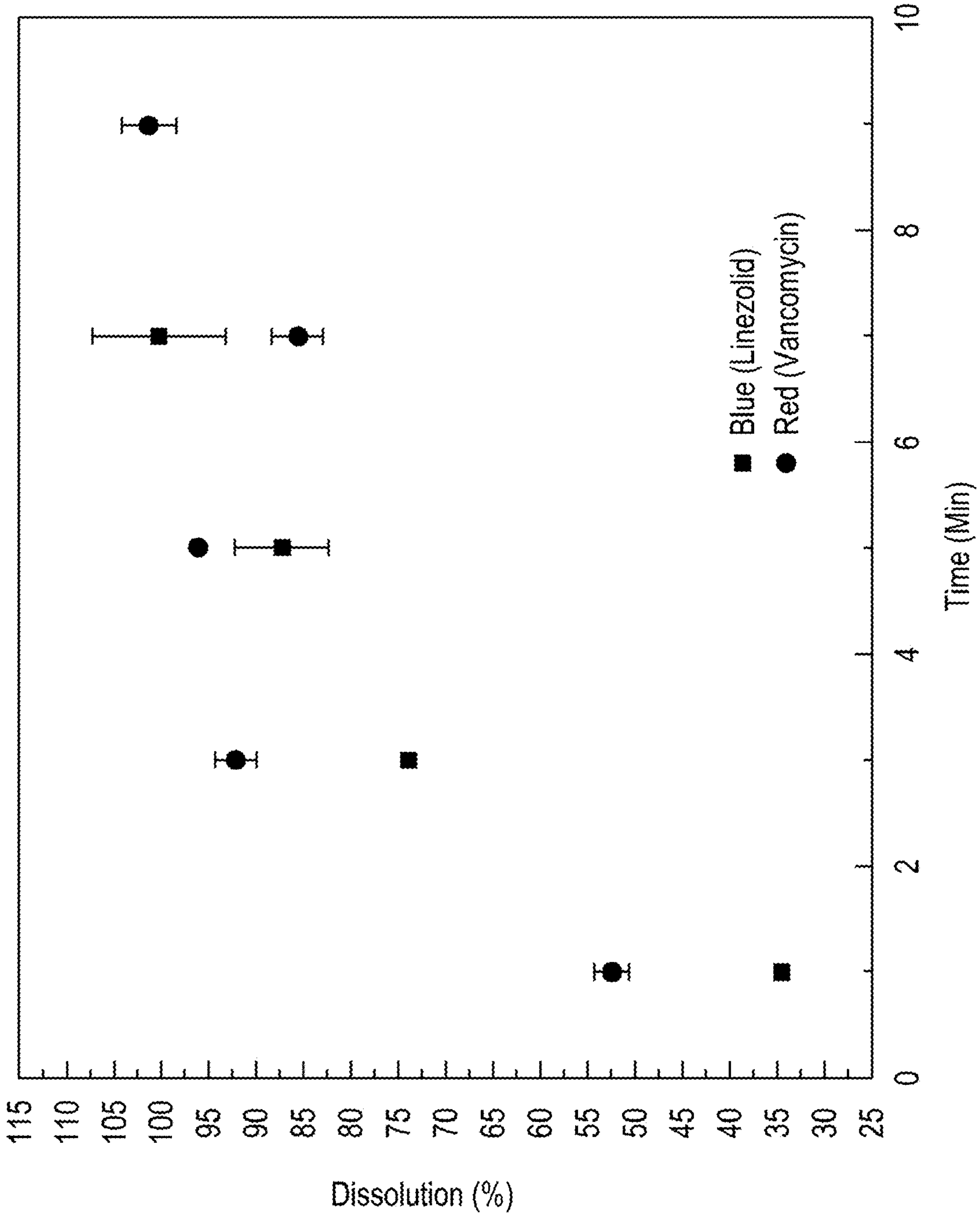
FIGS. 14A and 14B represent dissolution over time of both linezolid and vancomycin nanofibers in solution (FIG. 14A), and a comparison of critical dissolution (less than 80 percent) time for the nanofibers in liquid and gel media (FIG. 14B).

Optical absorbance measurements were taken from the fluid samples and compared to a fully dissolved sample reading. This data was then organized to show the dissolution percentage. As indicated in FIG. 14A, the dissolution rate for both the linezolid and vancomycin was high. The model linezolid nanofibers were observed to start dissolving faster, likely due to the smaller size, but the model vancomycin nanofibers reached full dissolution first (about seven minutes) due to the smaller mass of nanofibers that needed to be dissolved. Still, the linezolid nanofibers reached full dissolution after about nine minutes. This dissolution time scale can be considered negligible when compared to the total treatment length of about six hours or 360 minutes (1.9% and 2.5% of the total duration for vancomycin and linezolid, respectively).

Similar experiments were undertaken to measure the time required to dissolve the nanofibers on an agarose gel, which was used to mimic wound conditions. Gel dissolution testing was conducted using a low-melting temperature agarose gel dissolved in water to 0.5% w/w. The agarose was then pipetted in 1 mL samples into a 12-well plate and allowed to set. 1 $cm^2$ circles of blue (linezolid) nanofibers on the Al foil substrate were cut to shape using the laser cutter and placed on the gel surface. The first set of samples was removed after one minute, and then each following sample after an additional two minutes. Gel samples with dissolved nanofibers were then dissolved by heat exposure and stirred before 100 L samples were extracted and pipetted into a 96-well plate for optical reading using the spectrophotometer.

Figure 14B:
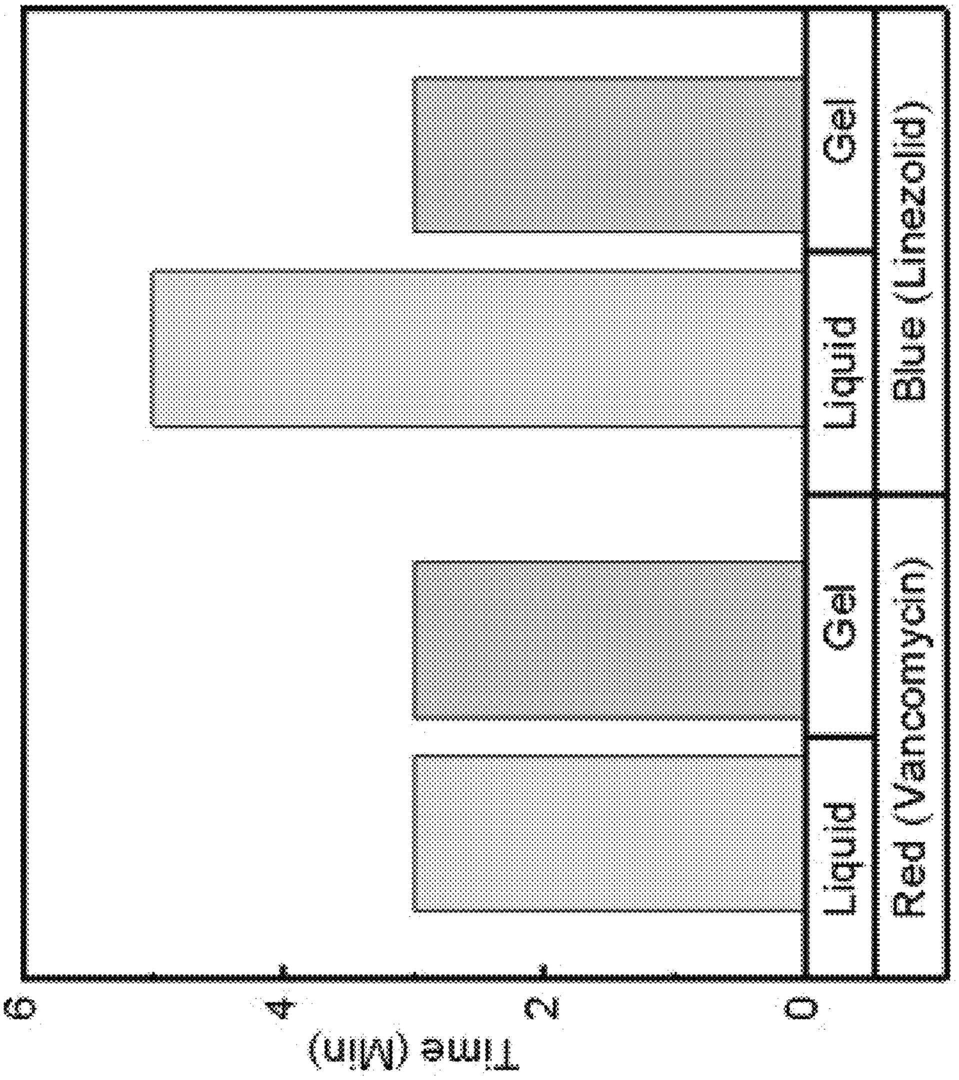

FIG. 14B shows the results which indicated a similar, rapid dissolution even into a semi-solid medium. The total dissolution measured and maintained for the red (vancomycin) nanofibers after just three minutes and the blue (linezolid) fibers after five minutes, which was again a negligible portion of the overall treatment time (0.8% and 1.4%, respectively).

Figure 15:
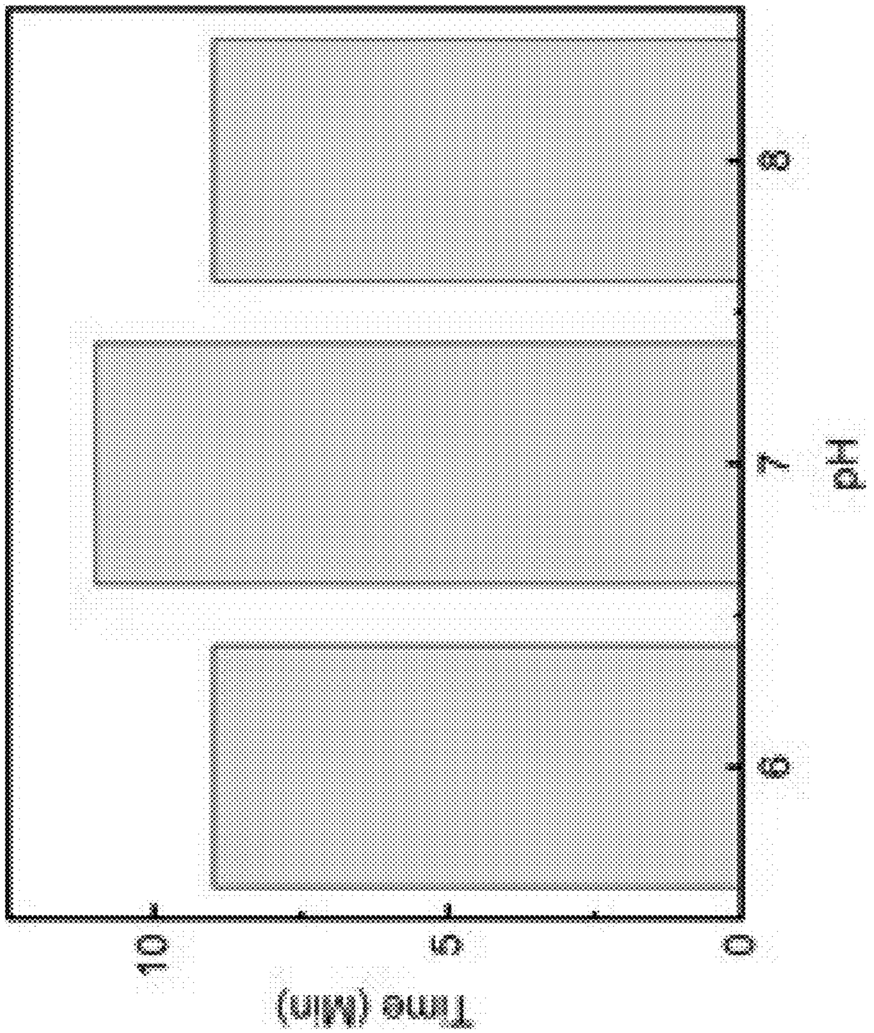
FIG. 15 represents a comparison of time needed to achieve critical dissolution of blue (linezolid) nanofibers in a buffer solution with varying pH values.

Because the pH found in an infected wound bed can vary, the dissolution over time of the blue (linezolid) nanofibers was characterized in solutions with three different pH values. The nanofibers were again cut to size and exposed to buffer solutions with pH values of 6, 7, and 8. FIG. 15 shows a comparison of time needed to reach critical dissolution (>80%) in each pH. It can be seen from the results that the pH of the solution had very little effect on dissolution time.

The impact of the adjunct therapy on bacterial infections is an indicator for its viability in treating infections. To show the positive impact of using the adjunct therapy, the ozone and antibiotic treatment was tested on stains of *P. aeruginosa*, a G−ve bacteria common in SSTIs.

To test the antibacterial effects of ozone in combination with antibiotics, a *P. aeruginosa* culture was inoculated in a solution of triptic soy broth (TSB) and incubated overnight. A sample of the mature culture was diluted in new TSB at 1:50. The new culture media was then pipetted into test wells in triplicate at 1:10 with either linezolid or vancomycin solution in phosphate buffered saline (PBS) at 200 μg/mL. The final solution in each well had a volume of 50 μL and a concentration of antibiotic of 20 μg/mL.

The bacterial samples were subject to the combination treatment of 100 ppm (4 mg/hr) ozone with vancomycin at 20 μg/mL and linezolid at 20 μg/mL. During testing, the test samples were kept at 37° C. At 2, 4, and six hours, 20 μL samples were withdrawn from the designated set of wells and plated on TSB agar plates. Bacterial colonies were counted after being incubated overnight at 37°. Experimental adjunct therapy samples were compared against treatment of only ozone, and control cultures exposed to antibiotics without the ozone.

Because both antibiotics in the test (linezolid and vancomycin) are designed to be effective against G+ve bacteria, it was expected that neither will show any effect against the bacterial strain unless combined with ozone. Additionally, treatment was administered to in vitro colonies of *P. aeruginosa* under ideal conditions for bacterial growth.

Figure 16A:
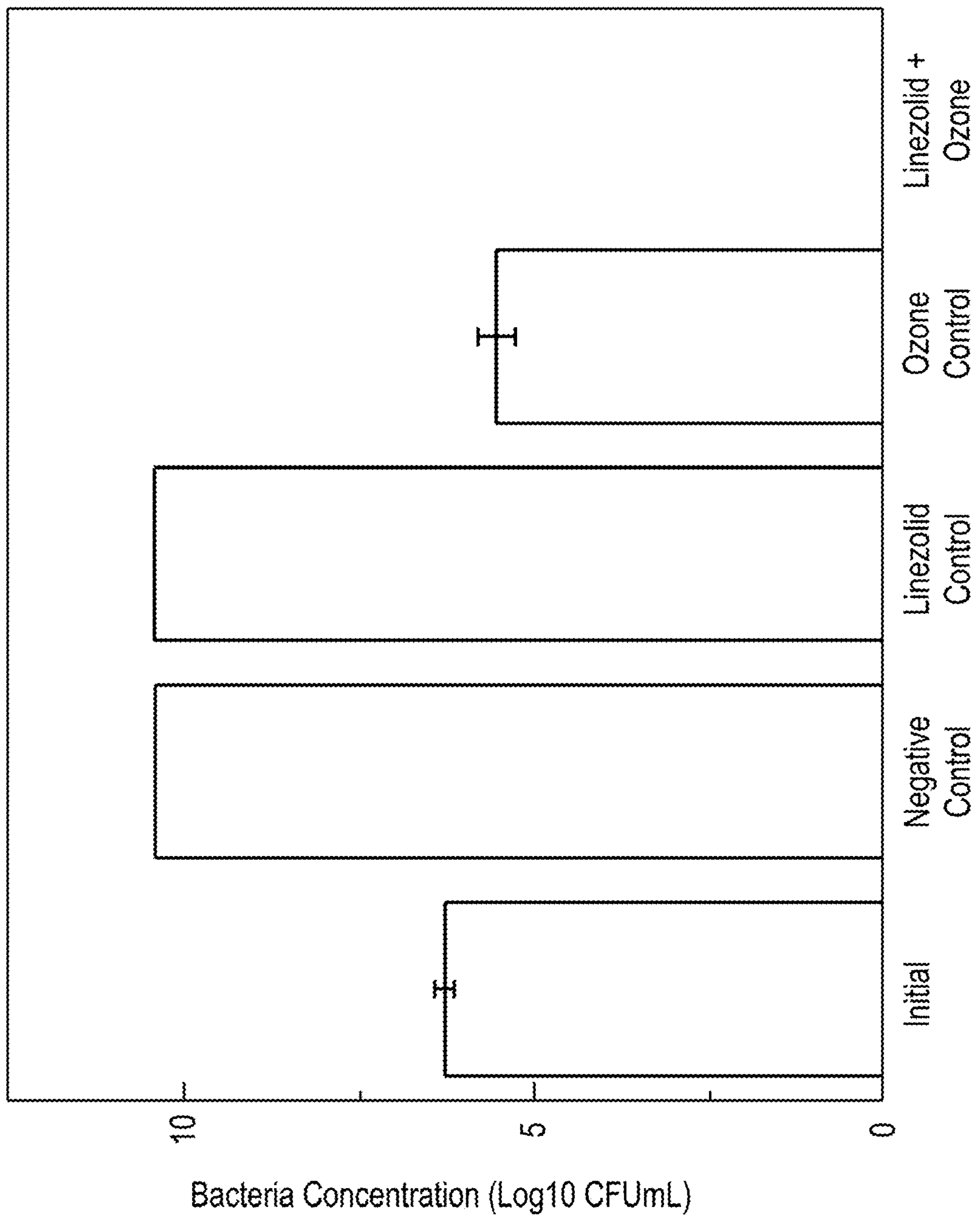
FIGS. 16A and 16B represent antibacterial results of ozone and linezolid adjunct therapy on *P. aeruginosa* after ozone was applied at 100 ppm for six hours and linezolid was applied in solution at 20 g/mL (FIG. 16A), and antibacterial results of ozone and vancomycin adjunct therapy on *P. aeruginosa* after ozone was applied at 100 pm for six hours and vancomycin was applied in solution at 20 g/mL (FIG. 16B).
Figure 16B:
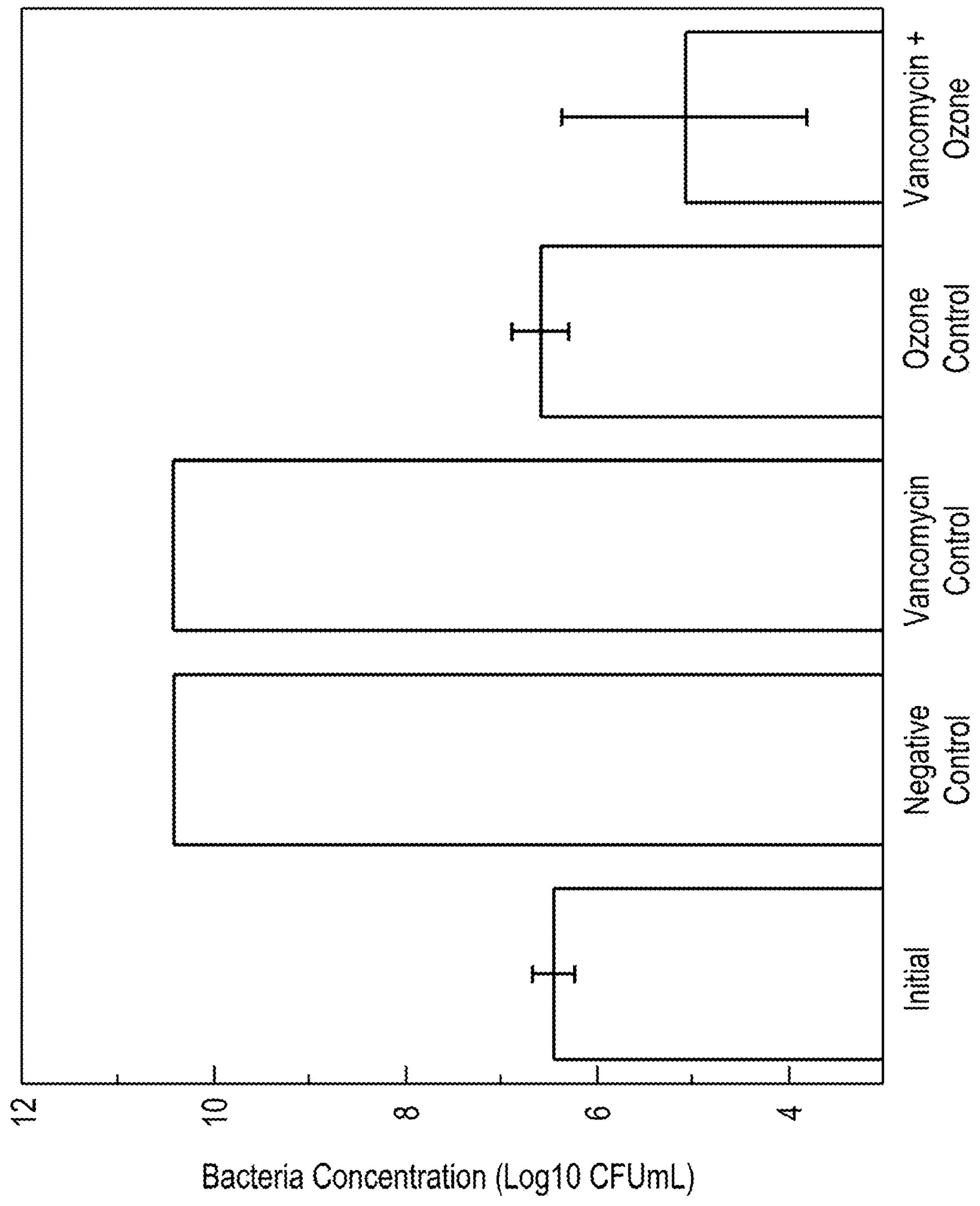

FIGS. 16A and 16B show the results of the antibacterial tests. FIG. 16A indicates that the adjunct therapy of linezolid and gaseous ozone showed a significant increase in antibacterial activity. When compared to the initial bacterial CFU/mL measurement, both the negative control (no treatment) and linezolid control (antibiotic only) showed significant growth in population. This shows that the linezolid antibiotic did not inhibit the growth of the bacteria at all as expected. The ozone sample, which was exposed to a 100-ppm ozone for six hours, showed a similar level of bacteria as the initial. This indicates that the ozone was able to kill off bacteria at about the same rate at which it reproduced but was not effective enough of its own to eliminate the infection completely. When combined with linezolid, the adjunct ozone therapy showed complete elimination of all bacteria. This indicates unexpected results in that the two treatments together are more effective than the sum of the parts.

Results for the vancomycin adjunct therapy tests (FIG. 16B) show a similar trend. Both the negative control and vancomycin control showed no impact on bacteria growth, and the ozone treatment response showed a similar result as well. The adjunct therapy using both ozone and vancomycin again showed a response that was better than the sum of the parts, though the treatment only reduced the number of bacteria by about 90% instead of complete elimination like was observed in the linezolid test.

Because the adjunct therapy showed strong antibacterial properties, the designed system was tested to ensure that it had no negative impact on human cells. By studying the biocompatibility, it was determined that the treatment system was both effective and safe to use. To test this, human keratinocyte cells were either exposed to the ozone therapy (with or without antibiotics) or left as a control. In each case, cell samples were exposed to test inhibitory concentration of the nanofiber solution containing either linezolid, vancomycin, or no antibiotic. Tests were conducted under the same six hour and 100 ppm ozone parameters as the antibacterial studies.

Figure 17A:
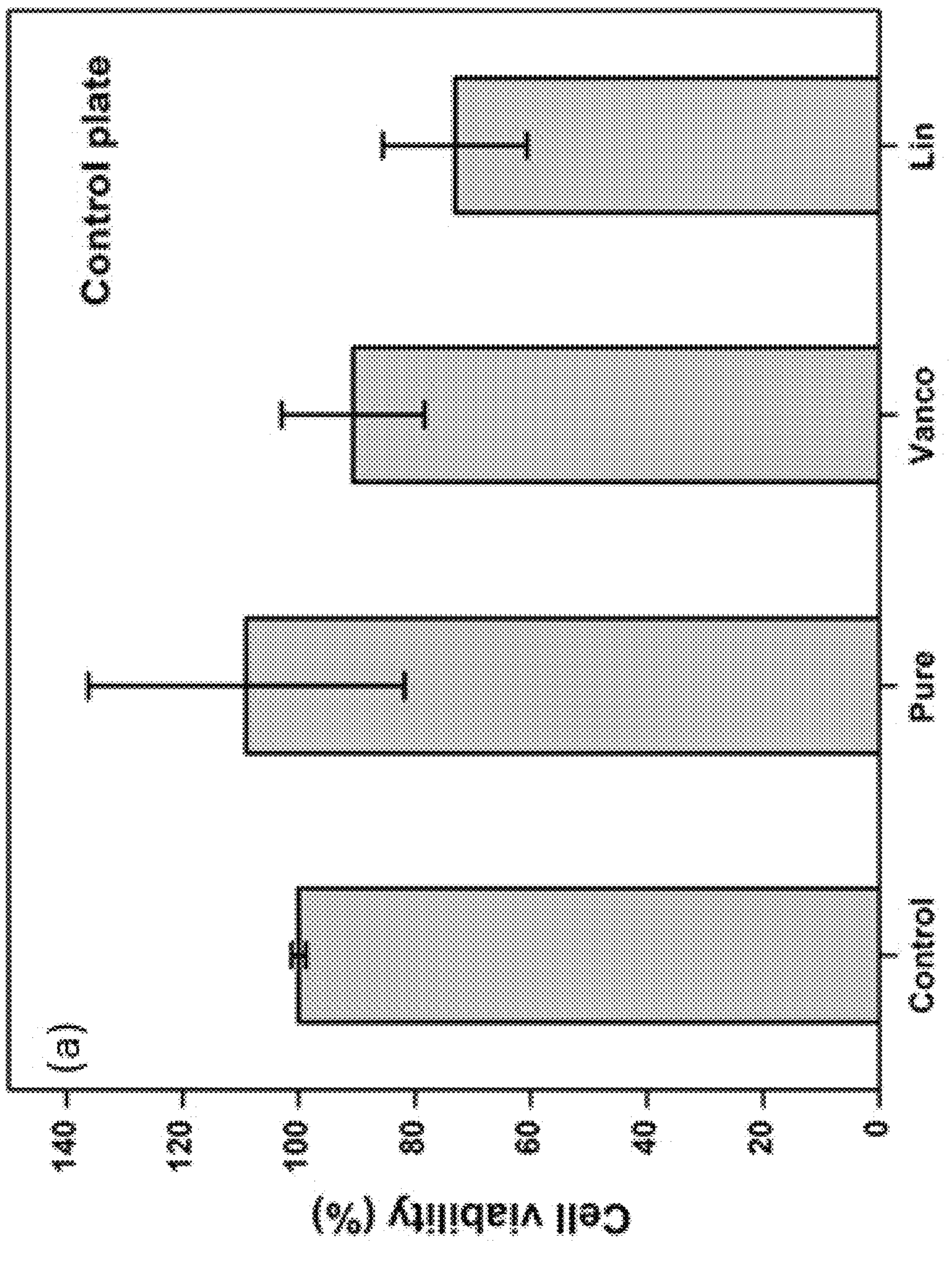
FIGS. 17A and 17B represent biocompatibility of adjunct therapy on human keratinocyte cells.
Figure 17B:
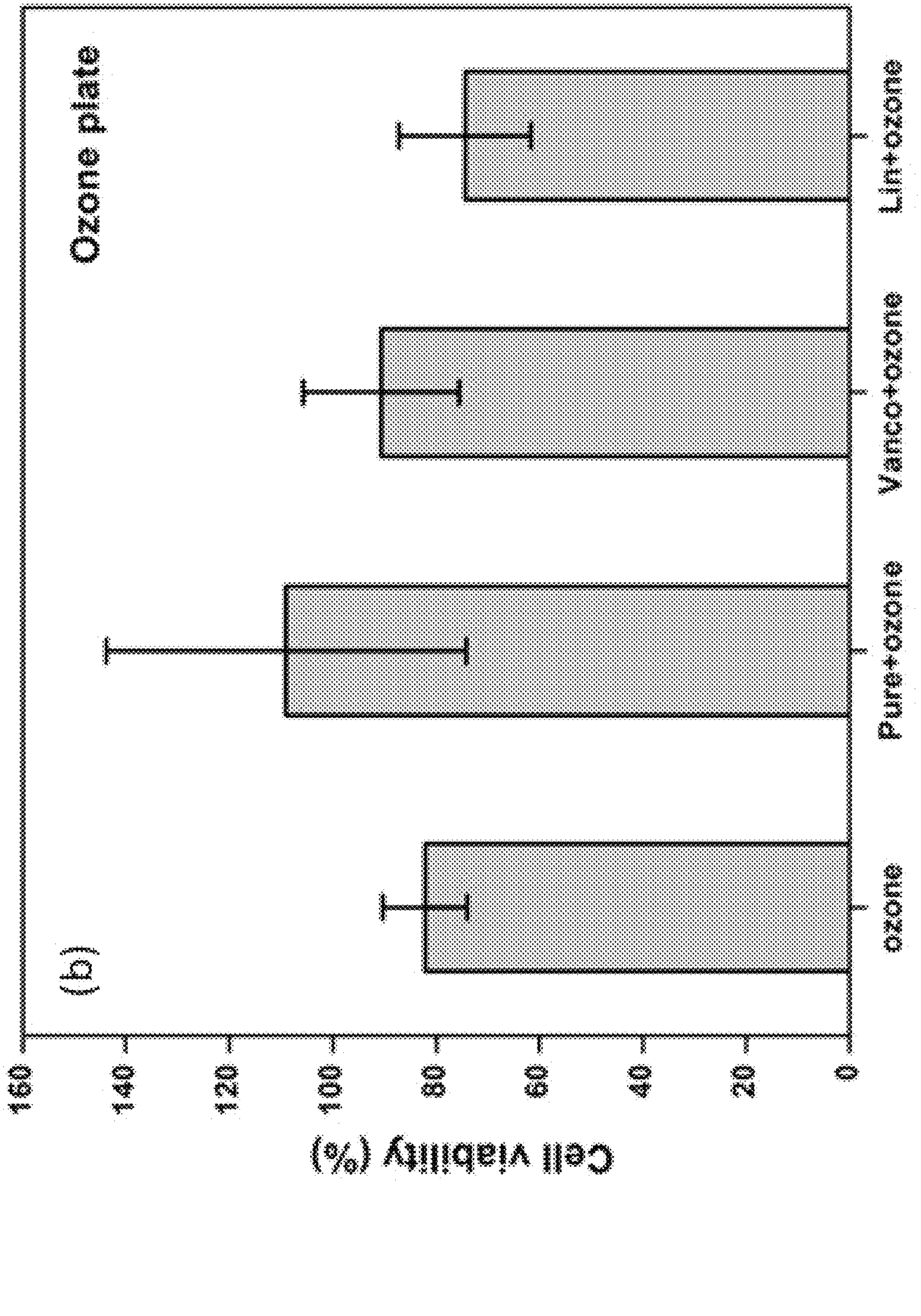

As represented in FIGS. 17A and 17B, the percent of cell viability did not significantly change when ozone was applied. The slight decrease in the cell viability with the use of antibiotics was constant with that with antibiotics and ozone. This showed that the adjunct therapy of the two treatments was just as safe as using topical antibiotics, but as seen previously, the antibacterial effects were significantly improved against previously resistive strains.

Antibiotic resistant infections are a growing public health concern. A promising alternative to antibiotic therapy is utilizing the antimicrobial properties of topical ozone treatments. It is believed that the portable ozone generation apparatus disclosed herein can apply ozone and/or antibiotics to a targeted area and thereby increase the options patients have in fighting infections that may otherwise be difficult to treat. As indicated by the above investigations, the patch 10 incorporated a hydrophobic and highly ozone permeable wound contact layer 18 and the intermediate dispersion layer 16 for increased gas distribution uniformity. The antimicrobial effects of the apparatus were tested against common antibiotic resistant strains of bacteria and the results indicated complete elimination of *P. aeruginosa* and significant reduction in the number of *S. epidermidis* colonies after six hours of exposure. These tests also showed a high level of biocompatibility (low cytotoxicity) with human fibroblast cells during the same duration ozone treatment. As such, the described patch 10 is a promising tool in the management of chronic infected wounds. The efficacy of combination therapies was also validated in vitro by using a combination of gaseous ozone and Gram-positive antibiotics to effectively treat otherwise resistant Gram-negative bacteria strains. These tests showed that the combination therapy was significantly more effective than either therapy alone.

While the invention has been described in terms of specific embodiments, it is apparent that other forms could be adopted by one skilled in the art. For example, the physical configuration of the ozone generation apparatus, ozone generating unit, and the patch 10 could differ from that shown, and materials and processes/methods other than those noted could be used. In addition, the invention encompasses additional embodiments in which one or more features or aspects of different disclosed embodiments may be combined. Therefore, the scope of the invention is to be limited only by the following claims.

The invention claimed is:

1. An ozone generation apparatus comprising:
- a flexible and porous gas permeable treatment patch configured to be releasably secured to a user's body such that an exterior surface of the treatment patch directly contacts skin on the user's body, wherein the treatment patch comprises:
  - a backing;
  - a wound contact layer that includes the exterior surface and defines exposed pores therein;
  - an intermediate flow dispersion layer enclosed between the wound contact layer and the backing, the intermediate flow dispersion layer being configured to promote uniform output flow from the exterior surface of the treatment patch;
  - a coating on the exterior surface of the treatment patch and comprising an antibiotic payload, the coating being configured to dissolve or degrade upon contact with ozone or with fluids at a wound site of the skin to release the antibiotic payload onto the wound site; and
- an ozone generating unit fluidically coupled to the treatment patch and configured to provide a flow of gaseous ozone through the exposed pores in the treatment patch toward the exterior surface of the treatment patch and then out through the exterior surface of the treatment patch.

2. The ozone generation apparatus of claim 1, wherein the exterior surface of the treatment patch exhibits hydrophobic properties to allow for contact with fluids without blocking the exposed pores thereof.

3. The ozone generation apparatus of claim 2, wherein the exterior surface of the treatment patch is coated with polydimethylsiloxane (PDMS) to exhibit the hydrophobic properties.

4. The ozone generation apparatus of claim 1, wherein the treatment patch includes a bonding layer securing the wound contact layer to the backing.

5. The ozone generation apparatus of claim 1, wherein the wound contact layer includes a synthetic Rayon-Spandex knit fabric.

6. The ozone generation apparatus of claim 1, wherein the coating includes water-soluble polymeric nanofibers having the antibiotic payload therein.

7. A method of treating a wound site on a patient, the method comprising:
- releasably securing a flexible and porous gas permeable treatment patch of an ozone generation apparatus to a user's body such that an exterior surface of the treatment patch directly contacts skin comprising the wound site on the user's body, wherein the treatment patch comprises:
  - a backing;
  - a wound contact layer that includes the exterior surface and defines exposed pores therein;
  - an intermediate flow dispersion layer enclosed between the wound contact layer and the backing, the intermediate flow dispersion layer being configured to promote uniform output flow from the exterior surface of the treatment patch;
  - a coating on the exterior surface of the treatment patch and comprising an antibiotic payload, the coating being configured to dissolve or degrade upon contact with ozone or with fluids at a wound site of the skin to release the antibiotic payload onto the wound site;
- generating gaseous ozone with an ozone generating unit fluidically coupled to the treatment patch;
- providing a flow of the gaseous ozone from the ozone generating unit through the exposed pores in the treatment patch toward the exterior surface of the treatment patch and then out through the exterior surface of the treatment patch such that the ozone contacts the wound site, wherein a uniform output flow from the exterior surface of the treatment patch is promoted with the intermediate flow dispersion layer; and
- dissolving or degrading the coating upon contact with the wound site to release the antibiotic payload onto the wound site.

8. The method of claim 7, wherein the treatment patch comprises a hydrophobic coating on the exterior surface such that the exterior surface exhibits hydrophobic properties to allow for contact with fluids without blocking the exposed pores thereof, the method further comprising reducing uptake of biofluids into the wound contact layer with the hydrophobic coating.

9. The method of claim 7, wherein the coating includes water-soluble polymeric nanofibers having the antibiotic payload therein.

10. The method of claim 7,
- wherein the portable ozone generating unit comprises an ozone generator and a micro-blower fan, the method further comprising:
- generating ozone in a sealed chamber with the ozone generator; and
- blowing the ozone produced by the ozone generator with the micro-blower fan from the sealed chamber to the treatment patch through tubing fluidically connecting an outlet of the sealed chamber to an inlet on the treatment patch.

11. The method of claim 7, wherein providing the flow of ozone comprises delivering a concentration of ozone to the wound site of below 0.6 g/mL.

12. The method of claim 11, further comprising delivering a concentration of ozone to the wound site of 0.2 g/mL to below 0.6 g/mL.

13. The method of claim 7, wherein the ozone generating unit is a portable ozone generating unit, the method further comprising mounting the portable ozone generating unit to the patient.

14. The method of claim 7, wherein the mounting comprises attaching the portable ozone generating unit to clothing worn by the patient.

* * * * *